United States Patent
Satyamurthy et al.

(10) Patent No.: US 9,481,705 B2
(45) Date of Patent: *Nov. 1, 2016

(54) MODULAR RADIOCHEMISTRY SYNTHESIS SYSTEM

(71) Applicant: THE REGENTS OF THE UNIVERSITY OF CALIFORNIA, Oakland, CA (US)

(72) Inventors: Nagichettiar Satyamurthy, Los Angeles, CA (US); Jorge R. Barrio, Agoura Hills, CA (US); Bernard Amarasekera, Winnetka, CA (US); R. Michael Van Dam, Los Angeles, CA (US); Sebastian Olma, Muenster (DE); Dirk Williams, Northridge, CA (US); Mark Eddings, San Pedro, CA (US); Clifton Kwang-Fu Shen, Westlake Village, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/941,164

(22) Filed: Nov. 13, 2015

(65) Prior Publication Data

US 2016/0130295 A1 May 12, 2016

Related U.S. Application Data

(60) Continuation of application No. 14/582,885, filed on Dec. 24, 2014, now Pat. No. 9,211,520, which is a division of application No. 13/058,526, filed as application No. PCT/US2009/004745 on Aug. 19, 2009, now Pat. No. 8,951,480.

(60) Provisional application No. 61/090,152, filed on Aug. 19, 2008.

(51) Int. Cl.
*C07H 19/16* (2006.01)
*B01J 19/00* (2006.01)
(Continued)

(52) U.S. Cl.
CPC ............. *C07H 19/16* (2013.01); *B01J 19/004* (2013.01); *B01J 19/126* (2013.01); *C07B 59/001* (2013.01);
(Continued)

(58) Field of Classification Search
CPC ............................. B01J 19/126; B01J 19/004
USPC ............ 422/186, 159, 105–116; 436/50, 55; 435/286.1, 3; 700/266
See application file for complete search history.

(56) References Cited

U.S. PATENT DOCUMENTS
5,759,513 A 6/1998 Nakazawa
5,972,711 A 10/1999 Barclay et al.
(Continued)

FOREIGN PATENT DOCUMENTS
EP 0510487 10/1992
JP 01139591 6/1989
(Continued)

OTHER PUBLICATIONS
Written Opinion and Search Report of International Application No. PCT/US2009/004745 mailed Jan. 19, 2010.
(Continued)

*Primary Examiner* — Shogo Sasaki
(74) *Attorney, Agent, or Firm* — Vista IP Law Group LLP

(57) ABSTRACT

A modular chemical production system includes multiple modules for performing a chemical reaction, particularly of radiochemical compounds, from a remote location. One embodiment comprises a reaction vessel including a moveable heat source with the position thereof relative to the reaction vessel being controllable from a remote position. Alternatively the heat source may be fixed in location and the reaction vial is moveable into and out of the heat source. The reaction vessel has one or more sealing plugs, the positioning of which in relationship to the reaction vessel is controllable from a remote position. Also the one or more reaction vessel sealing plugs can include one or more conduits there through for delivery of reactants, gases at atmospheric or an elevated pressure, inert gases, drawing a vacuum and removal of reaction end products to and from the reaction vial, the reaction vial with sealing plug in position being operable at elevated pressures. The modular chemical production system is assembled from modules which can each include operating condition sensors and controllers configured for monitoring and controlling the individual modules and the assembled system from a remote position. Other modules include, but are not limited to a Reagent Storage and Delivery Module, a Cartridge Purification Module, a Microwave Reaction Module, an External QC/Analysis/Purification Interface Module, an Aliquotting Module, an F-18 Drying Module, a Concentration Module, a Radiation Counting Module, and a Capillary Reactor Module.

16 Claims, 24 Drawing Sheets

(51) Int. Cl.
*B01J 19/12* (2006.01)
*C07B 59/00* (2006.01)
*C07C 201/06* (2006.01)
*C07D 207/46* (2006.01)
*C07H 5/02* (2006.01)
*C07H 19/06* (2006.01)

(52) U.S. Cl.
CPC .......... *C07B 59/002* (2013.01); *C07B 59/005* (2013.01); *C07C 201/06* (2013.01); *C07D 207/46* (2013.01); *C07H 5/02* (2013.01); *C07H 19/06* (2013.01); *B01J 2219/00049* (2013.01); *B01J 2219/24* (2013.01); *C07B 2200/05* (2013.01); *Y10T 436/115831* (2015.01); *Y10T 436/12* (2015.01)

(56) References Cited

U.S. PATENT DOCUMENTS

| | | | |
|---|---|---|---|
| 6,413,233 | B1 | 7/2002 | Sites et al. |
| 2004/0024493 | A1 | 2/2004 | Fagrell et al. |
| 2004/0028573 | A1 | 2/2004 | Schmitz et al. |
| 2004/0258615 | A1 | 12/2004 | Buchanan et al. |
| 2005/0233078 | A1 | 10/2005 | Boyd et al. |
| 2006/0191926 | A1 | 8/2006 | Ray et al. |
| 2008/0233653 | A1 | 9/2008 | Hess et al. |

FOREIGN PATENT DOCUMENTS

| | | |
|---|---|---|
| WO | WO03/078358 | 9/2003 |
| WO | WO2004/062779 | 7/2004 |
| WO | WO2006/134035 | 12/2006 |
| WO | WO2008/091694 | 7/2008 |

OTHER PUBLICATIONS

Lindsey, J.S., A Retrospective on the Automation of Laboratory Synthetic Chemistry, Laboratory Automation & Information Management, Elsevier Science Publ. BV., Amsterdam, NL, vol. 17, No. 1, Oct. 1, 1992, pp. 15-45.

Mangner, Thomas J. et al., Synthesis of 2'-deoxy-2'[18F]fluoro-B-D-arabinofuranosyl nucleosides, [18F]FAU, [18F]FMAU, [18F]FBAU and [18F]FIAU, as potential PET agents for imaging cellular proliferation, Nuc.Med. Bio., 30, pp. 215-224 (2003).

Pankiewicz, Krzysztof W. et al., A Synthesis of 9-(2-Deoxy-2-fluoro-B-D-arabinofuranosyl)adenine and Hypoxanthine. An Effect of C3'-Endo to C2'-Endo Conformational Shift on the Reaction Course of 2'-Hydroxyl Group with DAST1, J. Org. Chem. 57, 553-559 (1992).

Tann, Chou H. et al., Fluorocarbohydrates in Synthesis. An Efficient Synthesis of 1-(2-Deoxy-2-fluoro-B-D-arabino-furanosyl)-5-iodouracil (B-FIAU) and 1-(2-Deoxy-2-fluoro-B-D-arabinofuranosyl)thymine (B-FMAU), J. Org. Chem. 50, 3644-3647 (1985).

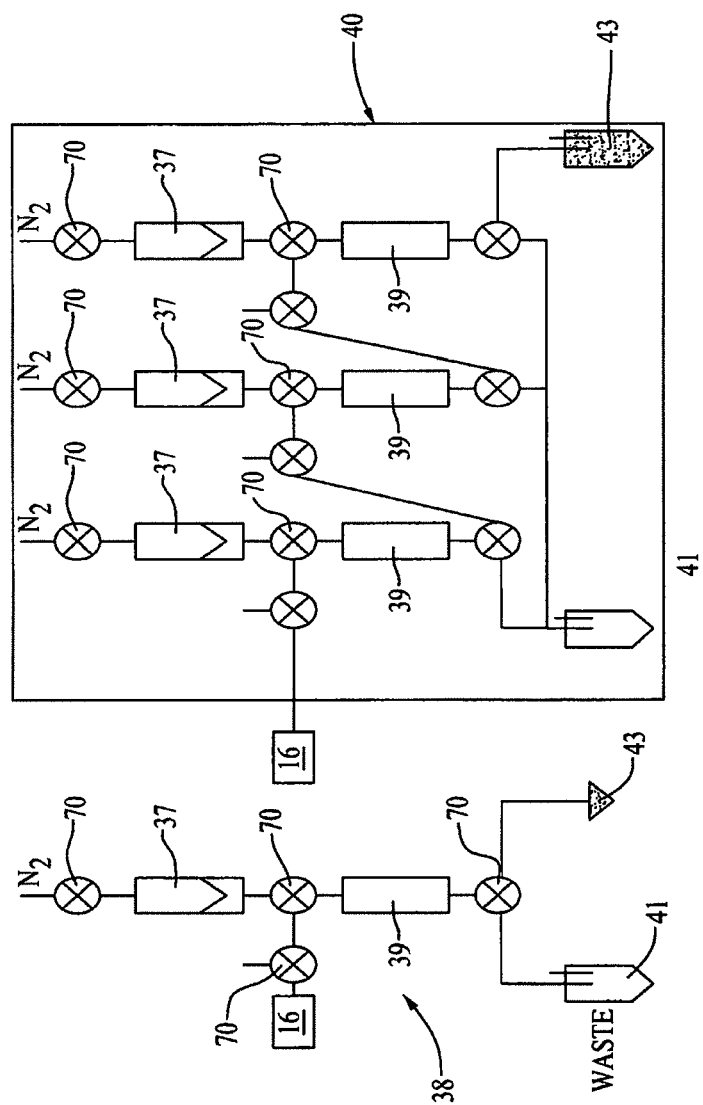

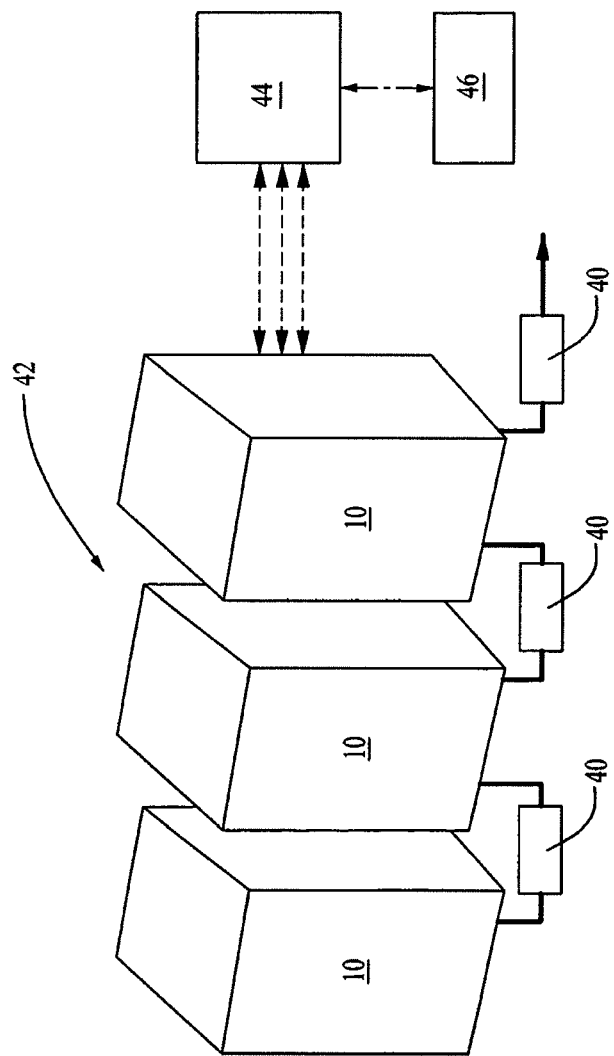

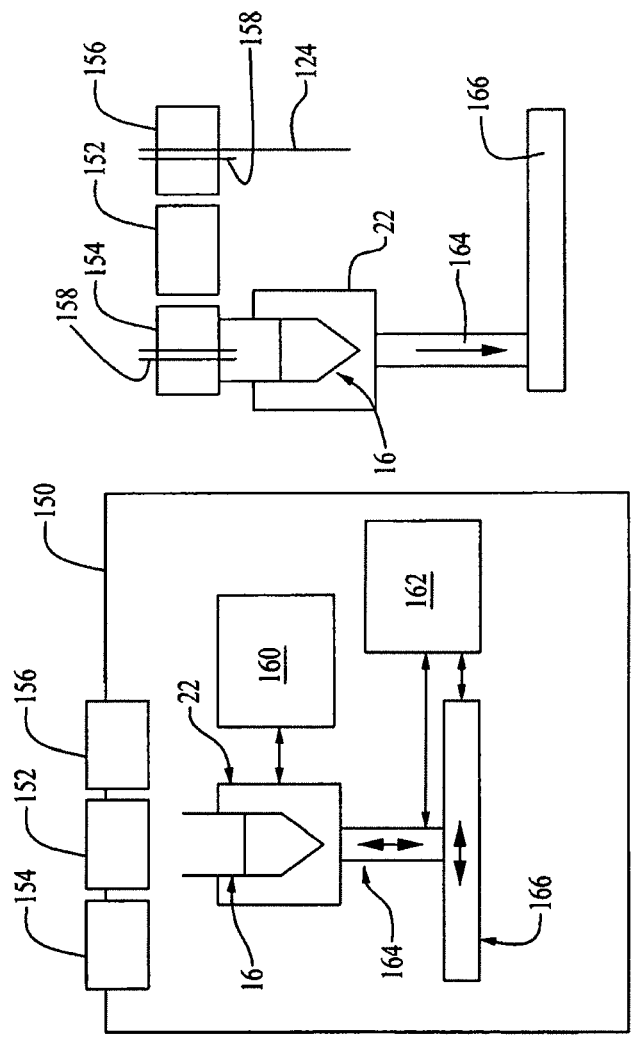

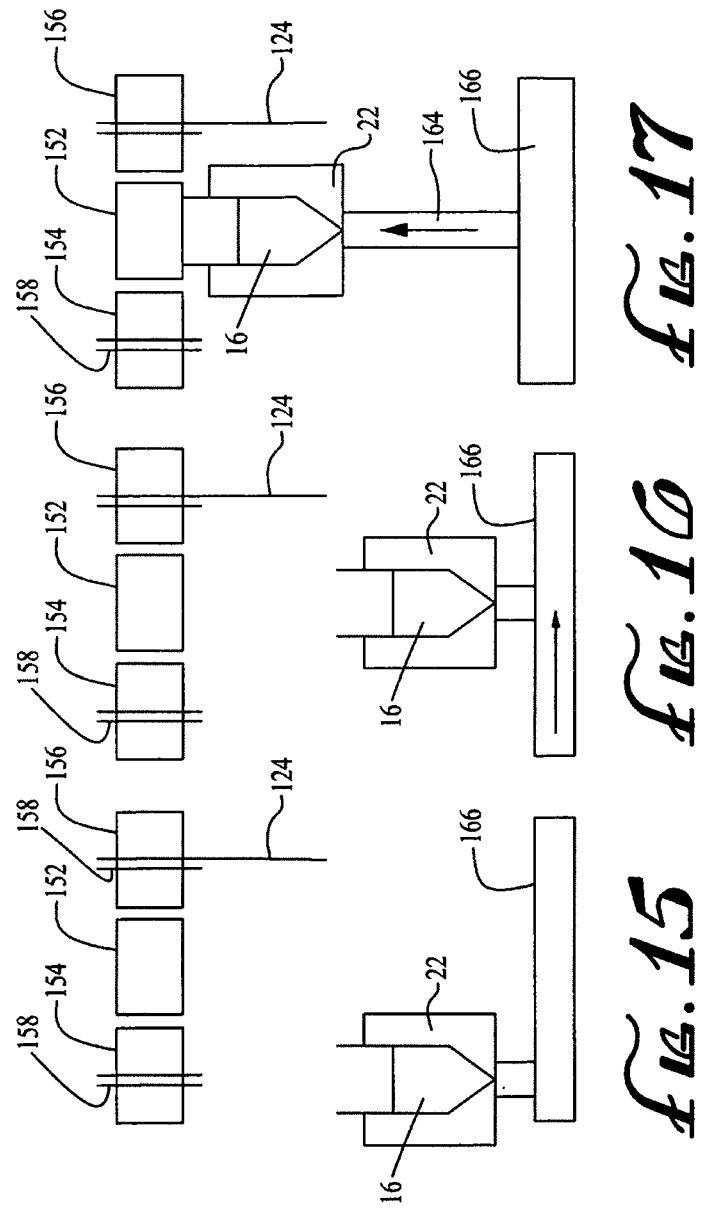

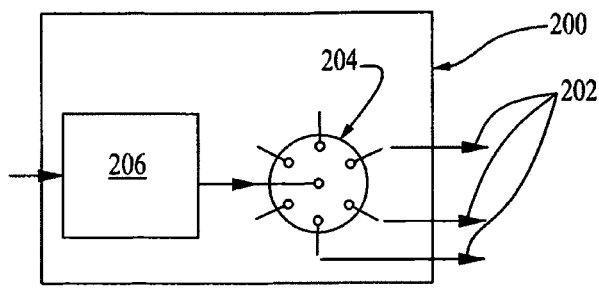
$fig.20$
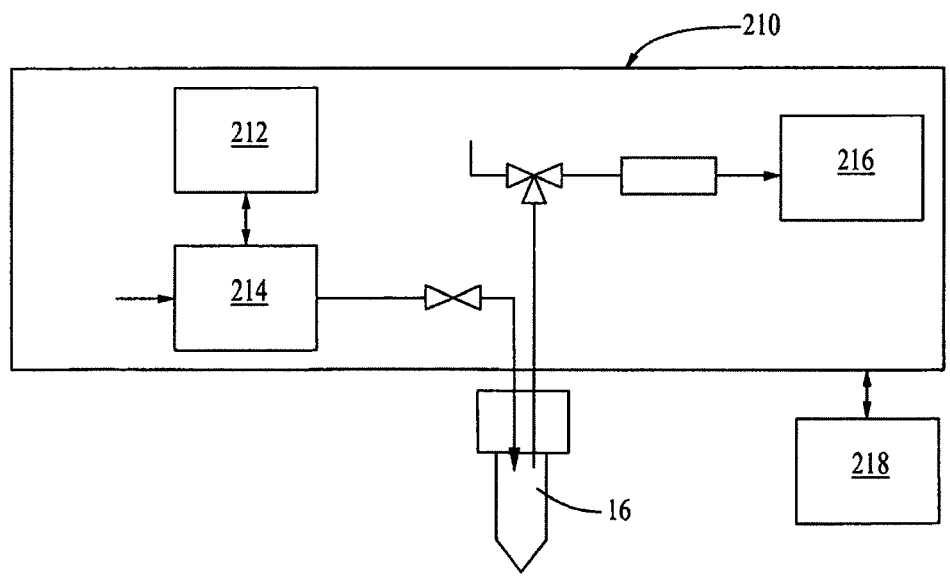
$fig.21$

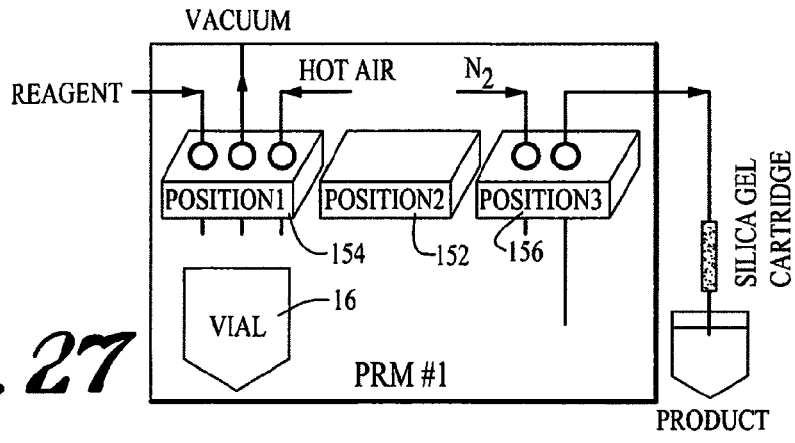
fig. 27
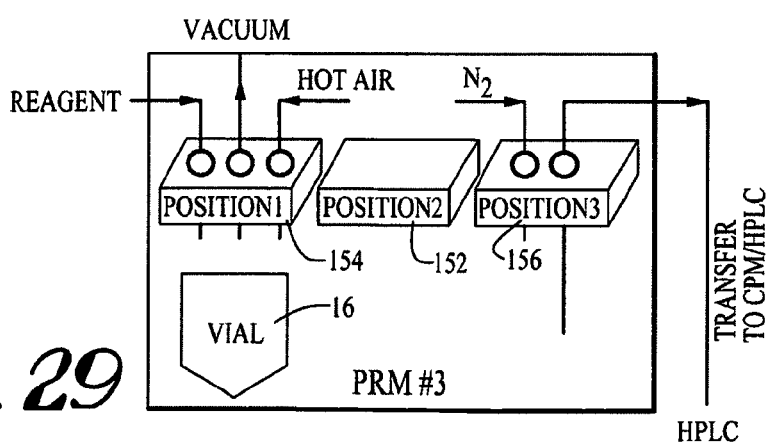
fig. 28
fig. 29

MODULAR RADIOCHEMISTRY SYNTHESIS SYSTEM

RELATED APPLICATION

This Application is a continuation of U.S. patent application Ser. No. 14/582,885 filed on Dec. 24, 2014, now U.S. Pat. No. 9,211,520, which itself is a divisional of and claims priority to U.S. patent application Ser. No. 13/058,526 filed on Jun. 2, 2011 now issued as U.S. Pat. No. 8,951,480, which itself claims priority to PCT Application No PCT/US2009/004745 filed Aug. 19, 2009 which claims priority to U.S. Application No. 61/090,152 filed on Aug. 19, 2008. The contents of the aforementioned applications are hereby incorporated herein by reference in their entirety. Priority to the aforementioned applications are hereby expressly claimed in accordance with 35 U.S.C. §§119, 120, 365 and 371 and any other applicable statutes.

STATEMENT REGARDING FEDERALLY SPONSORED RESEARCH AND DEVELOPMENT

This invention was made with Government support under Grant No. DE-FG02-06ER64249, awarded by the U.S. Department of Energy, and Grant No. CA086306, awarded by the National Institute of Health. The Government has certain rights in the invention.

FIELD OF INVENTION

Modular, automated chemical synthesis apparatus suitable for the preparation of small quantities of chemicals, particularly radio pharmaceuticals are described. The system and apparatus are also usable for preparing other compounds which may unstable or are desired in small quantities produced at the location they will be used.

BACKGROUND

Radiochemistry is a complex area of chemistry that is an increasingly important part of providing diagnostic imaging in the clinical setting. The growth in Positron Emission Tomography (PET) and Single-Photon Emission Computed Tomography (SPECT) means that researchers and clinical scientists are highly interested in synthesizing new diagnostic compounds and perfecting synthesis techniques for new radioisotopes, "tracers", "probes" and "biomarkers". However, because of the radioactive decay of the prepared materials, the hazard of radiation exposure to medical personnel, and the chemical instability of the radiolabeled materials, these radiation labelled compounds must generally be prepared on site and the diagnostic procedure conducted within a short period of time after the materials are prepared.

Radiochemistry has traditionally required manually intensive, bench top manipulation of chemicals with fairly standard chemical apparatus within an environment that is designed to protect the chemist from exposure of the fingers, hands, or body to radiation. Low-dose radiochemistry (<a couple of mCi) can be conducted in an appropriately reinforced fume hood with lead bricks and other types of passive shielding. High dose (curies) synthesis must be conducted in a hot cell with considerably higher shielding and safety requirements.

Manually-operated assemblies of reaction vessels, sensors, heaters, etc. are commonplace. Automated radiochemistry devices also exist (e.g., commercial FDG, methylation, etc.). However these devices are essentially optimized for a specific chemistry process and are not user configurable without having to physically manipulate hardware and reprogram the synthesis process. Existing radiochemical reaction systems are also generally not capable of performing high-pressure reactions (e.g. >50 psi).

A typical prior manual radiochemistry setup for performing radiochemistry experiments and synthesis of diagnostic materials comprises digitally-controlled hotplates and oil baths within a hot cell made of lead-bricks. Syntheses are generally followed by standard manual purification procedures.

Whether a low dose or high dose environment is involved, the increasing use of radiochemistry to perform synthesis with a variety of isotopes, including but not limited to $^{18}$F, $^{11}$C, $^{13}$N, $^{15}$O, $^{123}$I, $^{124}$I, $^{64}$Cu, $^{68}$Ga, etc. means that there is an increasing risk of radiation exposure to the chemist. Automated radiochemistry units are available, and several devices referred to as "automated synthesis modules" exist for specific types of reactions that are routinely and repeatedly conducted, including electrophilic chemistry, nucleophilic chemistry and methylation. However, these units are typically hard wired with a fixed component configuration for a specific number of reaction steps, solute volumes, and radiation levels and are notably inflexible for the experimental chemist or to handle multiple different end products. Such units typically are "black boxes" with pushbutton operation and must be physically rewired and the hardware and software reconfigured to perform a new or different synthesis step. This is in marked contrast to the visual and interactive prior art bench top manual apparatus.

SUMMARY

The modular radiosynthesis system which incorporates features of the invention consists of a sequence of subsystems or "modules", each of which performs a unit operation.

Each module includes control and telemetry capability so that it can be remotely controlled and monitored in a stand-alone fashion as well as readily assembled into a system to perform different reaction protocols. Stand-alone operation permits straightforward "plug-and-play" reconfiguration of modules without reprogramming, and requiring only fluid connections be made between modules to implement the desired sequences.

Modules are preferably constructed with a deep, thin profile so they can be stacked side by side in a compact space such as a mini-cell, while retaining an intuitive relationship between physical positions of modules and the sequence of steps in the radiochemical synthesis. Other stacking arrangements are also possible.

The apparatus enables extremely flexible chemistry to be conducted, "recorded" electronically and the replayed back in an automated fashion, including driving multiple units and some unique telemetry functions. The apparatus has particular utility as a research radiochemistry platform to provide easy synthesis of a wide range of compounds with little or no radiation exposure to the equipment operator. Because the platform is entirely remotely controllable, it can easily be configured to controllers and/or software for either manual or automated operation. Thus, the same platform can be used for synthesis development using manual control as well as for routine production by automatic control, thereby saving considerable development time that is normally needed to translate the optimized manual synthesis from a manual apparatus to an automated system.

While the description below is directed to a system incorporating various unit-operation modules to perform a complete synthesis of a purified end product ready for clinical use, including modules for storing and feeding in a controlled manner all of the required reactants and reagents, the modules themselves are unique devices, several of which are independently patentable.

BRIEF DESCRIPTION OF DRAWINGS

FIG. 7 is a schematic diagram illustrating operation in series of three SPE module.

FIG. 8 is a schematic diagram illustrating modularity with multiple individual reaction units arranged serially to provide an N-step reaction module.

FIG. 9 is a schematic representation of one embodiment of a reagent storage and delivery module.

FIG. 13 is a schematic representation of one embodiment of a high pressure robotic reaction module.

FIGS. 14, 15, 16 and 17 are schematic representations showing a moveable high pressure robotic reaction module in 4 alternative locations.

FIG. 20 is a schematic representation of an aliquotting module.

FIG. 21 is a schematic representation of a concentration module.

FIG. 27 is a schematic representation of a first reaction module in the fluorination step in a manual synthesis of [$^{18}$F] FAC.

FIG. 28 is a schematic representation of a second reaction module in the bromination and cytosine coupling step in a manual synthesis of [$^{18}$F] FAC.

FIG. 29 is a schematic representation of a third reaction module in the deprotection step in a manual synthesis of [$^{18}$F] FAC.

DETAILED DESCRIPTION

Figure 1:
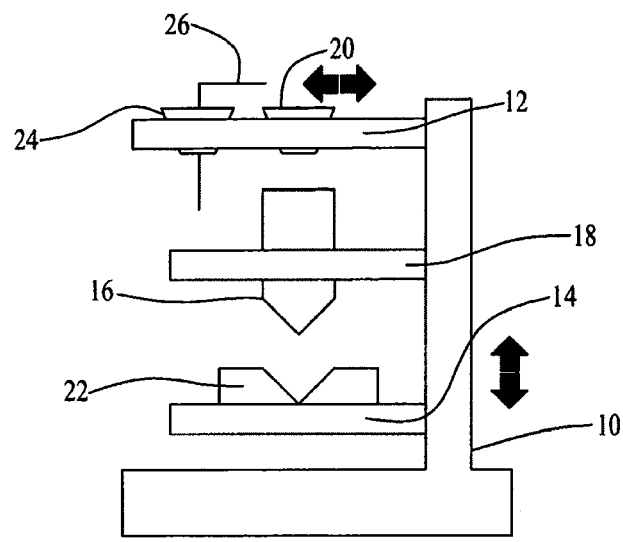
FIG. 1 is a schematic representation of a first embodiment of a robotic synthesis module also referred to as a reaction module, in its starting configuration incorporating features of the invention.

Disclosed are modular component assemblies referred to herein as "plug-and-play modules" that allow an operator to replace the manual "touch and see" mode of experimental synthetic radiochemistry and radiolabeling with a unit that can be controlled remotely from a radiation protected environment in an automated and repeatable manner. Specific advantages of the modular system include, but are not limited to:

a) A modular, n-stage robotics device that can be scaled infinitely through the addition of "generic" reaction modules to a provide a broad range of synthesis capability and address a broad range of reaction complexity. Each module or component of the system has its own control system and telemetry capability.

b) Incorporation of inexpensive but streamlined Solid-Phase Extraction (SPE) units for coordinating purification and QC of multi-step reactions.

c) Implementation of a unique robotic format that is both relevant and familiar to the chemist, but also facilitates a vessel pressurization function that supports high-pressure (>150 psi) reactions. No existing commercial automated synthesis units are capable of performing high-pressure radiochemistry.

d) Utilization of a "remote control" unit that is not limited to operation within a fume hood or hot cell. This unit allows streamlined control of each robotic actuator and SPE component utilizing, for example, cable telemetry, infra-red (IR) transmission through a lead glass viewing coupler, radio frequency (RF) telemetry, etc. Prior operations in fume hoods using hot cells are not capable of receiving an RF signal into a sealed unit because of radiation shielding. This remote control unit eliminates the risk of the chemist receiving "finger doses" of radiation during the syntheses process.

e) Utilization of remote sensing, including video, that limits the actuation range of the robotic arms for safety purposes as well as providing to the chemist a remote visual monitoring capability. This enables the chemist to either utilize the remote control at a position distant from the fume hood/hot cell (e.g., out of viewing range) or to integrate the control functions of the "remote control" with a more visual environment outside of the hotcell (e.g. video monitors, personal computers, etc.).

f) A "Macro" record function, which allows the user to manually execute a synthesis step with the unit, wherein the unit accurately records each actuation, washing, SPE, sequential reaction, etc. as a function of time. This synthesis can then be saved as a user preference or transmitted/shared with other users of a compatible apparatus elsewhere.

g) The functionality of the robotic control unit also includes "memo record" capabilities to include video, instrumental measurement of operating parameters (temperature, pressure, etc.) and voice annotations of a particular temporal event as a way of capturing expertise or research experience for laboratory notes or for building training/educational material into macros.

The collection of plug-and-play modules can be combined in different configurations to perform different syntheses. The modules are operatable in a stand-alone fashion (for integration with manual setups or other automated systems) or integrated into a central "master" control program.

A first embodiment of a device incorporating features of the invention as shown in FIGS. 1-4 comprises a remote controlled assembly 10, which includes robotic arms (two shown) 12,14 that can be moved up and down and forward and backward under remote control in order to perform pressurized reactions, solvent evaporation and product transfer (e.g. to another SPE unit).

The design incorporates a reactor vessel 16 sometimes referred to as a reaction vial 16 mounted on a fixed or removable arm 18. Mounted on the first robotic arm 12 is a silicone or Teflon septum or plug 20 or similar sealing unit capable of providing a tight seal for high pressure reactions. Also mounted on the first robotic arm 12 is a second plug 24 with tubular flow conduits 26 to allow delivery of liquid or gaseous reactants, the application of an inert atmosphere, and removal of solvents or end products. The assembly of components also allows for the application of pressure or vacuum to vessels from an external gas supply if desirable. The first robotic arm 12 can be moved such that the reaction vial 16 is open, or is sealed by one of the plugs 20 or 24. The heating block or oil bath 22 is mounted on the second robotic arm 14 so that it can be moved to within a desired distance from the reactor vessel 16 for very accurate computerized temperature control. Other aspects of the reaction system and the solid phase extraction (SPE) components are described below and illustrated in the other figures. It should be noted that the SPE components can be mounted on a rack or platform of the remote controlled assembly 10 for convenience and to reduce clutter, or can be a separate, stand-alone module.

The embodiments contemplate that the device can either be driven manually or remotely, where each axis of motion of the robotic arms 12,14 (including the heating unit) may be fractionally adjusted. Alternatively, through the use of limiter devices and specific sensory components, not shown, (e.g., light beams, microswitches, proximity sensors and integrated pressure/temperature transducers) the assembly and individual components can be controlled using a computer interface to perform specific operational command functions, such as "heat reaction vessel for 3 minutes at 120° C.".

Figure 2:
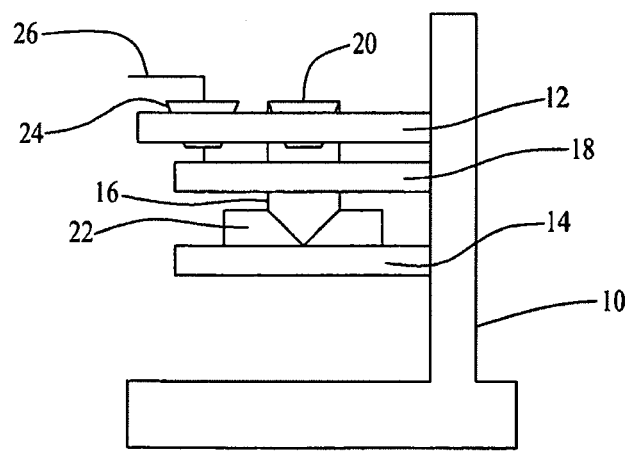
FIG. 2 is a schematic representation showing the configuration of the robotic synthesis module of FIG. 1 during a representative reaction under pressure.
Figure 3:
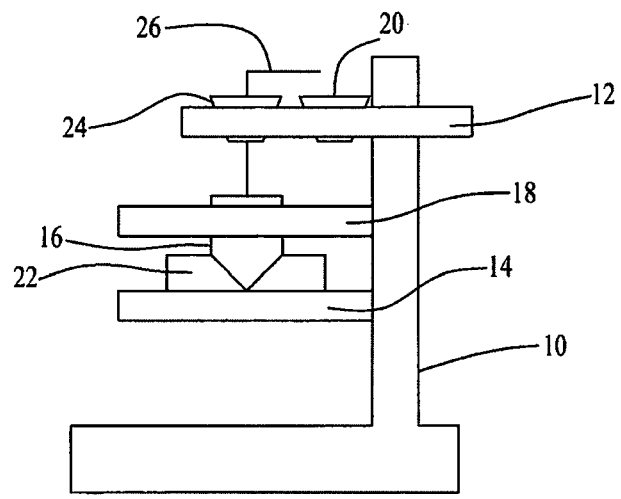
FIG. 3 is a schematic representation showing the configuration of the robotic synthesis module of FIG. 1 during a representative reaction solvent evaporation stage.
Figure 4:
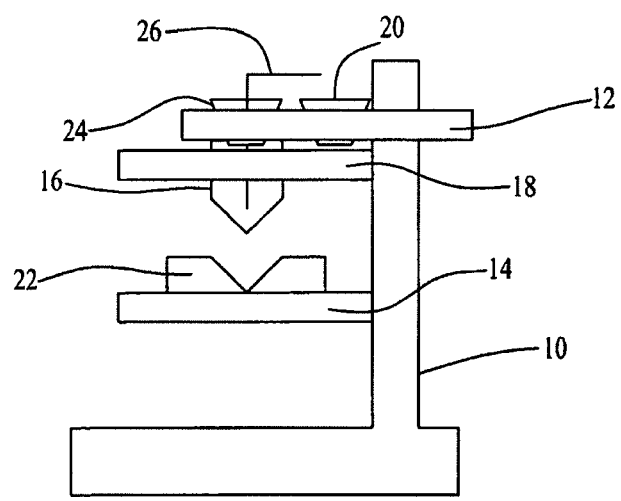
FIG. 4 is a schematic representation showing the configuration of the robotic synthesis module of FIG. 1 during a product transfer, which may also include flushing and washing out of the reaction vessel.

FIGS. 1-4 are schematic and functional representation of the robotic synthesis assembly with the modules in different functional operational modes, allowing the reactants to be added to the reaction vessel and the vessel to be sealed so that the reaction can be performed at desired temperatures, combinations of temperatures or temperature ranges and pressures for desired periods of time. FIG. 1 shows the reaction module 10 prior to implementation of a reaction procedure. FIG. 2 shows a pressurized, closed reaction vessel 16 with the second robot arm 14 and heater block 22 raised to heat the vessel and the first robot arm 12 lowered with the plug 20 sealing the vessel. FIG. 3 shows a subsequent stage, wherein the sealing plug 20 has been replaced by the second plug 24 for performing, using the flow conduit 26, a solvent evaporation procedure at the completion of the reaction, which can still be under heating, if required. The vessel 16 can then be remotely opened for product transfer or the contents of the vessel can be flushed and/or washed out of the vessel 16 through the same tubular conduit 26 as shown in FIG. 4.

In a preferred embodiment elevated pressure is generated in the reaction vessel as a result of heating and vaporizing a solvent or other liquid placed with the reactants in the vessel instead of pressurizing from an external source. It has been found that high pressures developed in the reaction vessel using an external source can create unexpected problems. For example, referring to FIG. 5, high pressures can be applied to the reaction vessel using nitrogen gas fed through the $N_2$ manifold 30. However, due to pressure limitations of the valves 70 and sealing limitations of the inlet lines in the stopper assembly the reaction vessel may tend to leak or the reactants in the reaction vessel can be pushed into the tubes 36 extending into the reaction mixture. This may result in inadequate heating or mixing of the reactants, cross-contamination with reagents added at later times, or loss of reactants and leakage of radioactive materials to the surrounding area. Commercially available reaction equipment are generally limited to ~50 psi pressures and any attempt to increase the pressures beyond that leads to the problems described above. In the modular reaction assembly described herein, pressurizing of the reaction vessel is preferably not pressurized using an external gas source so as to avoid these problems. Instead, pressure inside the reaction vessel 16 is generated from vaporization of the materials within the vessel by controlling the temperature of the vessel. To prevent leaking or excessive loss of solvent the reaction vessel is sealed with silicone or Teflon stoppers. These easily hold high pressures, and no tubes extend into the vessel during the reaction. In that manner pressures of >100 psi can be generated and maintained without problem and without loss of the solvent or reactants. After the reaction is completed, the reaction vessel is opened from a remote location and appropriate tubings are applied to the vessel and placed into the solution in the reaction vessel for transfer out using vacuum or pressure. All these operations can be accomplished remotely without risk of radiation exposure to the operator.

Figure 5:
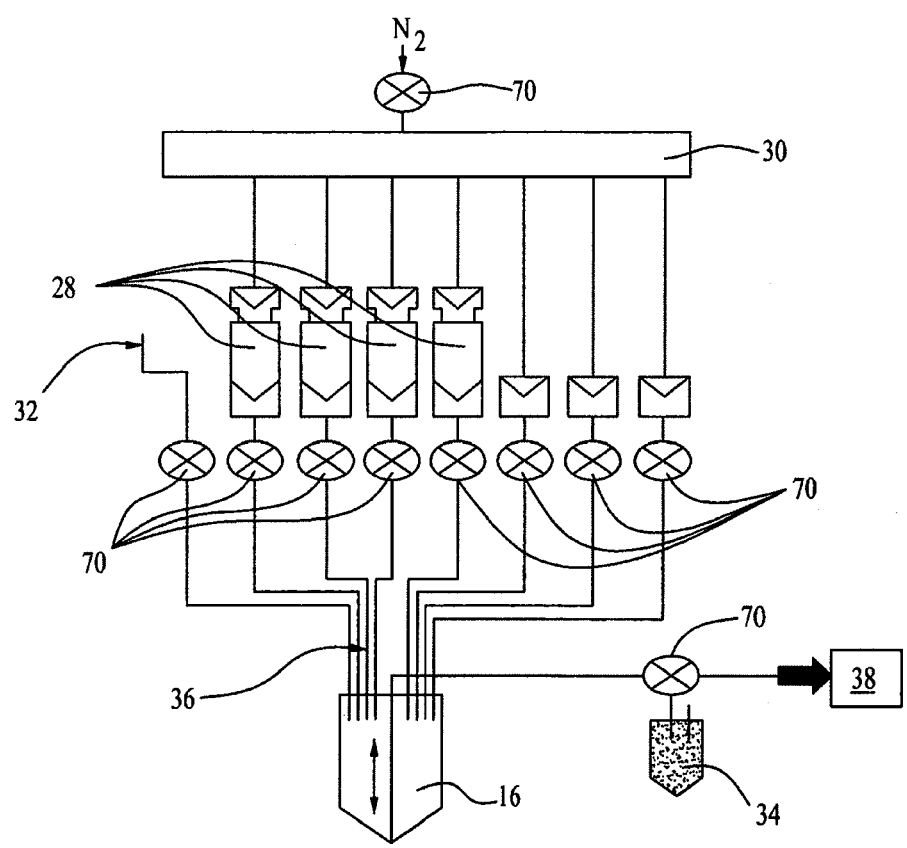
FIG. 5 is a schematic diagram of the single reactor unit of FIGS. 1-4 with the reaction vessel connected to various operational components and material feed sources.

FIG. 5 is a schematic diagram of a single reactor vial 16 showing the connections to reagent reservoirs 28, pressurized gas in the $N_2$ manifold 30, prior reactor feed 32 and wash, waste, and product recovery 34. Each of the feed and withdrawal lines 36 entering the reactor vial 16 are represented by the tubular flow conduit 26 in the prior figures.

(For ease of visualization, the plug 24 is not shown in FIG. 5). The valves 70 connect to each source of feed material.

Figure 6:
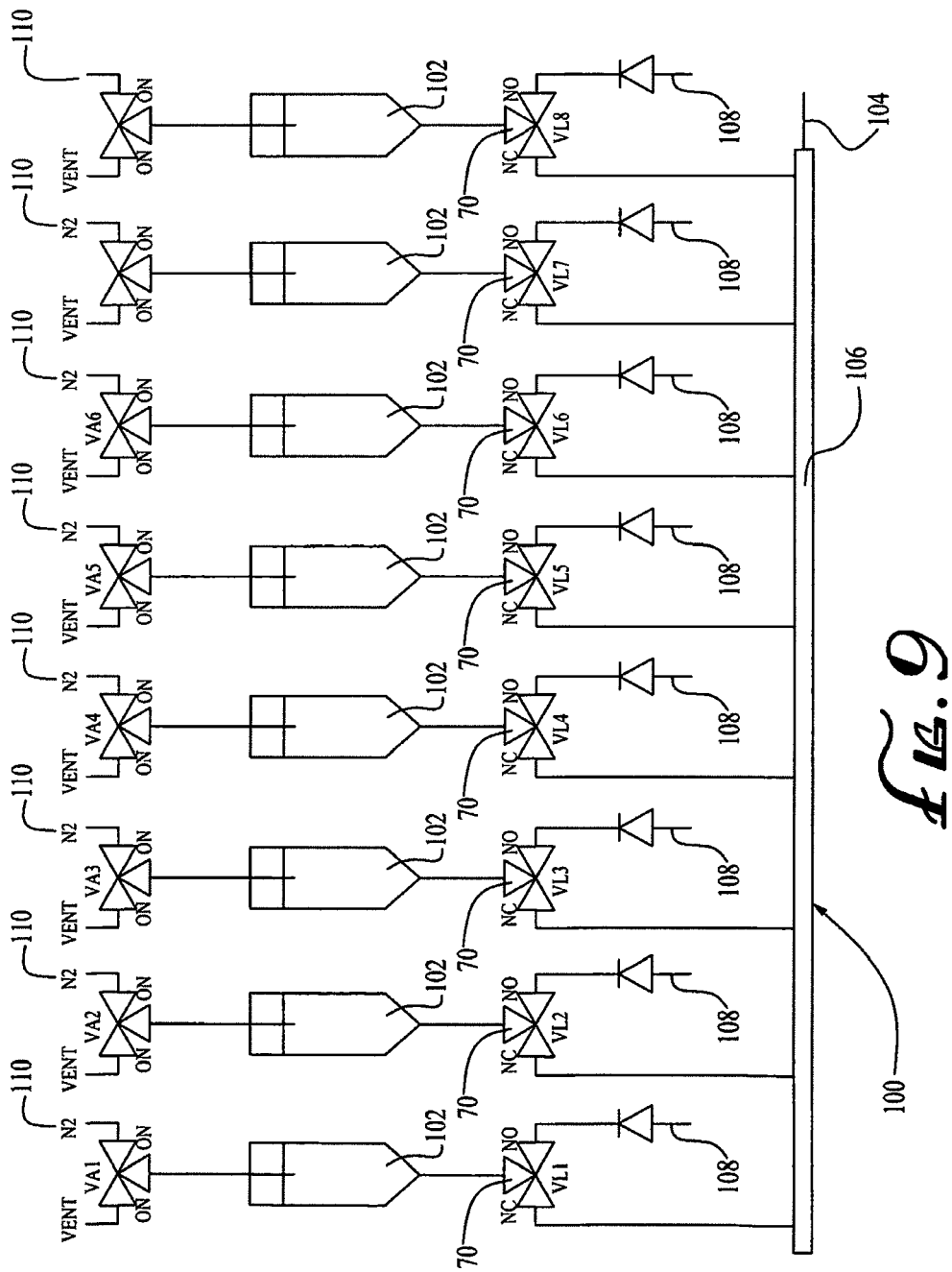
FIG. 6 is a schematic diagram of a single Solid Phase Extraction (SPE) module.

FIG. 6 is a schematic diagram of a single Solid Phase Extraction (SPE) unit 38 for use to recover the reaction products from a reaction module such as reaction module 10. It should be noted that the SPE can either be a single step purification unit 38 or, as shown in FIG. 7, a multi-step separation system 40. Typical components of the SPE are an eluent chamber 37 and a separation cartridge 39 providing a waste stream 41 and a purified product stream or product collection chamber 43. The addition of a reservoir of wash solution to wash the cartridge after trapping, and the addition of a cartridge regeneration/activation subsystem are also contemplated.

A unique advantage of the modular system described herein is that it can be infinitely scaleable. An arbitrary number of reaction vessels each with their own controllers and telemetry can be "stacked" together to provide an n-stage reaction with SPE stages inbetween. This concept is illustrated in FIG. 8 which shows multiple individual remote controlled reactor assemblies 10 in series with single or multistage separation modules 40, 42 between the reactor assemblies 10 to provide an N-step reaction module 42. Fluid/reagent lines are modular and neatly interfaced to the units for low clutter. Each unit, as well as the assembly, can be preprogrammed or manually interfaced through a control unit 44 with a computer 46 to control and monitor the process.

If the modular robotic synthesis device is to be used in either a fume hood (with some degree of "retro fit" for low-dose radiation handling) or in a hot cell (for larger doses), different control line adaptations may be required. However, the system enables the operator to perform sophisticated experiments and material production without radiation exposure. In many instances, the control may be facilitated directly by a cable running through the hot cell/fume hood door or access ports. However, in cases where the radiation shielding is completely sealed, telemetry (not shown) may also be performed, for example using IR/LASER transmission through a lead glass viewing port. In general, telemetry may be facilitated by cable, IR/LASER communications (including visible/line of site), RF, including techniques such as conventional MHz remote control (e.g. 27 MHz), BlueTooth, Cellular, WiFi and other proprietary formats. Where IR/LASER communication is performed through the lead-glass viewing port of a hot cell, it may also be desired to provide an optical coupler mounted on each side of the glass.

The controller assembly may be configured in various standard arrangements including a dedicated control box with various levers and switches to intuitively control the radiochemistry synthesis system modules or may take the form of a touch screen or touch tablet PC that has an instrumentation interface relevant to the configuration of the robotics or the configuration of the chemical operations, or other means used for remote control of equipment. Preferred aspects of the control system include:

a) Limit sensors to ensure that the device operates at safe temperature, pressure, stirring speeds, and other operating parameters, and that ranges and component movement are not exceeded, thus streamlining user settings/actions.

b) Real-time data acquisition of all the motions and operating conditions logged against a time stamp for the purpose of "recording" procedural actions of "macro" and "memo" functions for repeating and duplicating the reaction procedure.

c) An "emergency" stop, which de-pressurizes and/or lowers the reaction temperatures and conditions and stops the robotic units, in case of a malfunction.

d) Temperature, pressure, radioactivity, time, etc. sensors for accurately recording the conditions within each reaction vessel.

e) "Macro" functions, for recording a series of reaction events in individual and an N-module radiochemical synthesis system to establish "presets" so that the procedure can be re-run without user intervention.

f) "Memo" functions, so that the user can create a "snapshot" of reaction conditions (sensor input), including a video record and a record of voice memo/text comments, the memos being stored as part of a laboratory annotation system and distributed along with a "Macro", for example, for educational/training purposes and to aid in repeating procedures and reactions.

Aside from the sensor data which captures the reaction information and the streamlined utilization of modular remote control assemblies 10, it is also contemplated that the system includes a digital capture of video information. A small video camera (not shown) can be focused on the reaction vessel or vial 16. A "ceiling" view camera (not shown) for observing each robotic arm 12, 14 as well additional video cameras (not shown) for viewing other components of the system can also be included. This enables the system operator to be physically located at a distant from the apparatus. This also enables:

a) Routine functions to be performed (e.g. pre-recorded macros) while being remotely monitored b) Several units running different production activities to be placed within a single hot cell, thus optimizing production space c) "Tele-chemistry" applications, so that several users at different locations can collaborate for an experiment, or individuals at a second location can observe.

d) "Master/slave" operations can be conducted whereby an operator conducts an experiment at a first location and a slave unit at a second location performs a duplicate of the first operation. This can provide added production capabilities, confirm reproducibility and be used in training scenarios.

Operable module systems have been constructed and have been used to synthesize numerous compounds on a routine basis. Using the apparatus and systems described above, examples of the synthesis of several radioactive labeled materials and the operating conditions for each are described below following the more detailed descriptions of the several different modules Examples of additional modules incorporating features of or usable in the invention described below include but are not limited to a reagent storage/delivery module (RDM), cartridge purification module (CPM), high pressure robotic reaction module (PRM), microwave reaction module (MRM), external QC/Analysis/Purification Interface Module (APIM) aliquotting module (AM), drying module (DM), concentration module (CM), radiation counting module (RCM) and a capillary reactor module (CRM).

Reagent Storage/Delivery Module (RDM)

The RDM module 100 contains multiple fluid storage reservoirs 102 that can accept reagents during the setup process, prior to the introduction of radioactivity into the system. These reagents are stored until needed during the synthesis, and then delivered by remote control to the RDM output 104. In some embodiments, the RDM includes provisions for certain reagents (e.g. unstable, or air-sensitive reagents) to be loaded into the module just prior to their use in the synthesis. For example, tubing connected to the loading port of the RDM can extend outside of the radiation-shielded environment to permit injection of freshly-prepared reagents for immediately addition to the reaction vial.

In a preferred configuration, valves 70 are mounted on a reagent manifold 106 to minimize the number of fittings and tubing, which improves reliability and reduces problems due to human error. A first embodiment of an output configuration of the RDM has all of the reservoirs 102 connect to a common output channel (FIG. 9). FIG. 9 shows an RDM 100 with eight reservoirs 102 connected through valves 70 to a delivery manifold 106. Connected to each reservoir 102, through the valve 70 is a reactant feed 108 for the required reactant, so the reservoirs can be filled with the appropriate quantity of reactant for each reaction. Connected to the top of each reservoir 106 is a pressurized gas feed 110 to drive the reservoir contents into the manifold 106. One skilled in the art will recognize that the reservoir's contents can be delivered by other means such as feed pumps or drivers for plungers in each reservoir, for example a syringe pump system. All of the valves are remotely controlled for delivery of the appropriate reactants at the appropriate time to the reaction vial 16.

In another embodiment such as shown in FIG. 5 each reservoir has an independent output port connected to the vial 16. The needs of a particular radiosynthesis process dictates which one is required, for example if two reagents are incompatible and carryover is important the second embodiment is preferred. Alternatively, a hybrid configuration with some reagent reservoirs connected to a shared channel and some connected to individual output ports can be used.

In one embodiment of the RDM, eight external reservoirs are connect by Luer® fittings on the top of the manifold. These vessels can be off the shelf reservoirs made of plastic, glass, etc. and typically have volumes ranging from a few mL to 25 mL. Reagents are delivered by gas pressure in the headspace above the reagent. This is controlled via 3-way solenoid valves that can pressurize the headspace or vent the pressure. The use of inert gases in pressure and vent systems is contemplated for processes where reagents are sensitive to air, moisture, etc. For ease of operation the volume can be pre-measured into each reservoir and the entire volume delivered.

In a second embodiment multiple reservoirs can be machined directly into the manifold. This eliminates the majority of the fittings and tubing needed. In this embodiment, the maximum reagent volume was selected to be 3 mL, sufficient for the vast majority of radiosyntheses. This embodiment was designed to facilitate automated cleaning after use. Cleaning should be performed immediately after synthesis to avoid drying of feed solutions that can create particles (e.g. salts) that impede proper future valve function. Cleaning solutions can be introduced via the gas pressure system, can be added through an additional filling port, or can be loaded from the module output.

In a further embodiment the manifold is replaced with a microfluidic chip having integrated microvalves for greatly reduced losses, dead-volume, and carryover. Storage volumes could also be much smaller.

In an embodiment with eight reagent storage sites the reagents are dispensed through a common fluid manifold 106 to a specified location. The RDM includes inert check valves (Bio-Chem, New Jersey) for reagent loading, inert three-way valves (SMC, Japan) for switching between the common inlet and reagent loading, and a machined manifold fabricated from Ultem® polyether imide (SABIC Innovative Plastics, Pittsfield, Mass.) to provide the common outlet (FIG. 9). Storage reservoirs used in the RDM can comprise commercially-available empty, disposable SPE cartridges, or glass reagent vessels. Each reservoir attaches to the Ultem® manifold through a Luer-Lok® fitting. The initial reagent loading is also accomplished through a Luer-Lok connector that is connected to the check valve. The reservoirs are pressurized at the capped end to dispense the stored reagents.

Functional testing of the RDM was undertaken using common reagents used in radiochemistry (Acetonitrile, DMSO, etc.). Reagents were added and dispensed in a repeated fashion to determine loading and dispensing efficiency. The efficiency was determined by testing performed with F-18, to measure the amount of liquid not dispensed or left behind in each component of the RDM (fittings, reservoir, etc.). Each component was placed in a dose calibrator to determine the amount of F-18 not transferred through the manifold. Each measurement was compared to the final dispensed amount in order to track all of the F-18 activity. Carryover was measured by dispensing radioactive solution from one position, then a non-radioactive solution from a second position, and measuring the amount of radioactivity in the fluid from the second dispensing operation.

Cartridge Purification Module (CPM)

Figure 12:
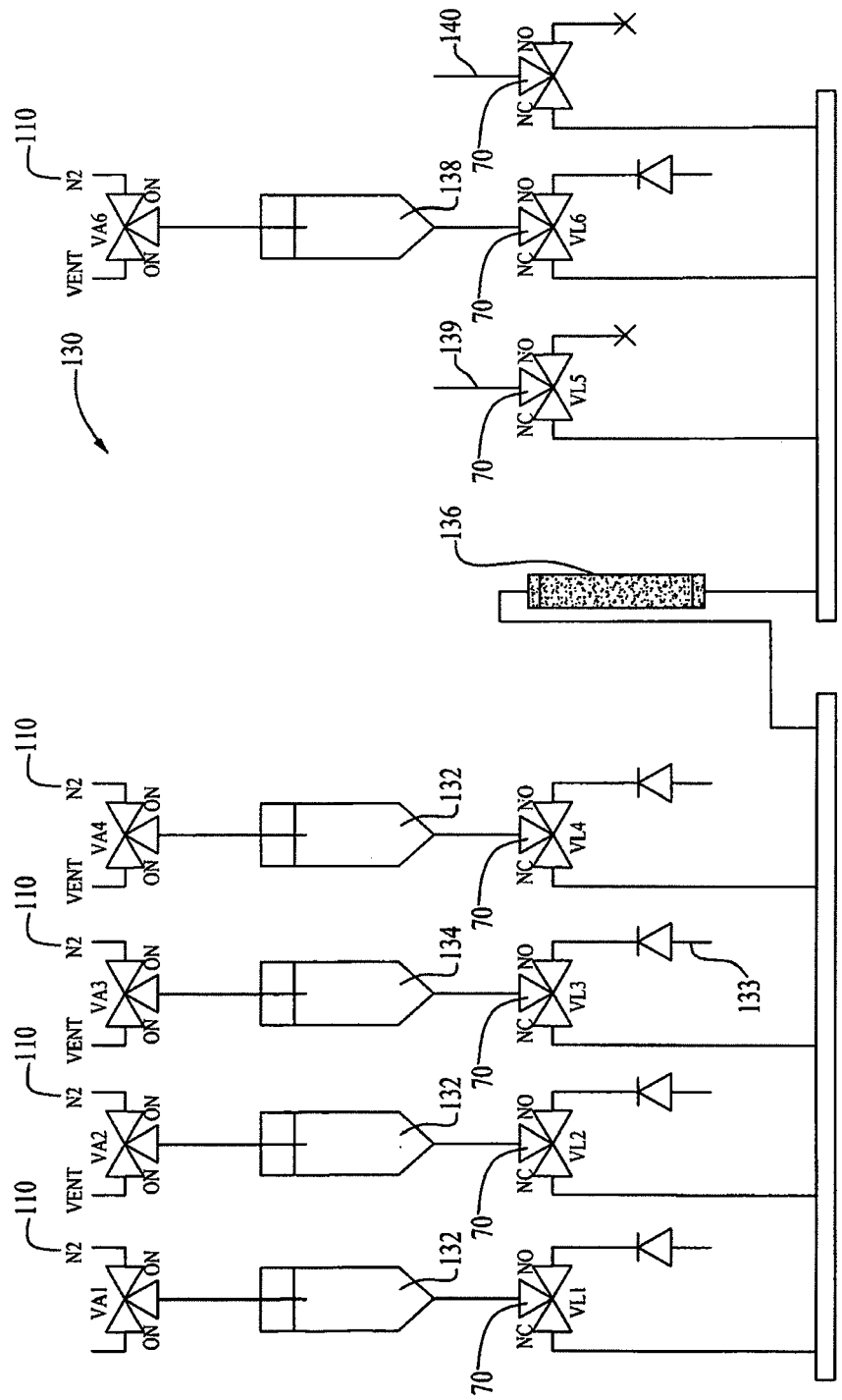
FIG. 12 is a schematic representation of one embodiment of a cartridge purification module.

The CPM 130 shown in FIG. 12 is designed to perform a variety of cartridge purifications, generally consisting of the trapping the desired product on a solid support, washing away contaminants and then eluting the desired product from the solid support. Alternatively, the CPM can also perform 'filtering' operations. The CPM includes reagent storage reservoirs 132 for diluents (to dilute the sample before passing through the cartridge, e.g. 1:10 or 1:20 in water), washing, and eluent solutions along with controlled means to feed these reservoirs. The CPM also includes an inlet port 133 for the unpurified sample, a cartridge 136 (e.g. pre-activated), a waste output 140, a mixing reservoir 138 and a collection output 139 that is connected to the next module. Contents of reagent storage reservoirs can be directed to flow through the cartridge with appropriate configuration of valves and activation of pumps (or gas pressure). Fluid flowing through the cartridge can be collected or directed to waste by appropriate configuration of valves.

In one embodiment valves are included in a manifold to minimize the number of fittings and tubing. The dilution, wash, and eluent reservoirs are connected via a valve to a common channel which is connected to the purification cartridge 136. The output of the cartridge is connected to valves for selection as to whether the flow goes to the waste 140 or collection (output) port 139.

A second embodiment has two optional features: (i) an additional reagent reservoir of activating solution to perform cartridge activation just prior to the separation, and (ii) an empty reservoir 138 at the cartridge outlet into which the eluate can be loaded and mixed (e.g. by bubbling) to eliminate the concentration gradient as the sample comes off the cartridge. This may be useful depending on the downstream module. For example, a capillary reaction module would have better performance if the entire solution has a uniform concentration.

Alternative designs use external reservoirs or embedded reservoirs as described above for the RDM, as well as a microfluidic implementation can be used.

FIG. 12 shows one embodiment of the CPM. The chemical being purified is fed to product reservoir 134 initially containing a diluents (e.g. water). After delivery of the chemical by gas pressure, additional flow of gas causes bubbling that mixes the chemical with the diluent. The diluted chemical is then caused to flow through the purification cartridge 136. In purifications where the desired compound is trapped, the cartridge is then treated with wash solution from a reagent reservoir 132, and partially dried to remove the majority of liquid. The untrapped chemical solution and wash solution are directed to the waste port 140 after passing through the cartridge. The product is released by flowing an eluant (also from a reservoir 132) to transfer the purified product to the output 139, where the product is collected or is delivered to the next module in the radiosynthesis system.

The CPM is similar to the RDM in its basic design. However, the fluid path is slightly different as a purification cartridge 136 is placed in line with the common outlet. Reagent storage reservoirs 132 are connected through Luer-Lok® ports for easy assembly and removal. The cartridge 136 is also assembled in the same manner. Reagents for elution, wash, or other purposes can be loaded and delivered through chemically-inert 3 way valves 70. Loading of the reservoirs 132 is accomplished by feeding through a chemically inert check valve 70. Delivery of the reagents is accomplished from a pressure source 110 supplied to each reservoir. Functional testing was performed as previously described for the RDM. Solutions containing F-18 were passed through all of the functional components to identify the overall loss of activity.

High-Pressure Robotic Reaction Module (PRM)

The main components of the PRM 150, shown in FIGS. 13-17 are a vial 16 in which the reaction occurs and a heat transfer unit 22, also referred to as a reaction vessel or heater/reaction vessel. The PRM has an inlet port to accept the production solution from the previous module (e.g. a purification module or a reaction module), if one exists, and an outlet port connected to the next module in the system.

This PRM is designed to perform high-pressure reactions (typically during superheated conditions when the reaction mixture is heated far above the solvent boiling point). A reaction "step" may consist of several processes: adding reagents to the vial and mixing, heating (often under sealed conditions to avoid evaporation), and transfer of product out to the next module. Evaporation of solvent before and/or after the chemical reaction may also be performed. The transfer step usually requires a dip tube 124 present during the reaction or a retractable tubing/needle (a removeable dip tube 124) that can be introduced later into the vial 16. However, fixed dip tubes 124 are undesirable when high-pressures are used due to problems described previously, and retractable needles or tubing have reliability concerns.

Commercially available liquid valves can rarely exceed pressures of about 50 psi, unless high-pressure "rotary" valves are used. In a preferred embodiment the valves are isolated from the reaction pressure by using robotics to move the vial 16 into a "sealed" configuration (with no paths in fluid connection with valves) during the high temperature reactions, and then move it into "ported" configurations when fluid transfers in and out are needed. In the sealed configuration no valve is exposed to the pressure inside the reaction vial 16; only the sealing mechanism is exposed to elevated pressure. As a result, the above problems are avoided.

In a first embodiment of this module, shown in FIG. 1-4, the reaction vial 16 remains in a fixed position. A heater 22 (e.g. oil bath) can be moved up to heat the reaction vial 16 and back down to cool the vial 16 (e.g. air cooling). Two or more stoppers 20, 24 can be robotically positioned (e.g. a 2-axis motion system) to seal with the vial to perform the various operations. The first stopper 20 is typically a plug or cap, while the other stoppers 24 typically have tubing 26 connected to them to introduce reagents, perform mixing (bubbling), and to draw product out of the vial 16 after the reaction.

In a second embodiment shown in FIG. 13, the heater/reaction vessel 22 moves so the fluidic interfaces remain stationary. This design accommodates fluidic interfaces which may include several pieces of tubing 158 connected to other modules in the system. Motion of these parts would create the potential for this tubing to become tangled, detached, or even damaged. To avoid the risk of failure due to these factors, it is preferred to move the heater/reaction vessel 22 instead. The vial 16 is mounted within a thermally-conductive (e.g. metal) heat transfer block so the temperature of the vessel can be controlled at all times via active heating (e.g. resistive) and cooling (e.g. air, cool gas, or liquid). A temperature sensor/controller 160 monitors the temperature inside the metal heater block (calibrated to the liquid temperature inside the vial) to perform closed loop feedback control of the temperature via an integrated temperature controller. Other means of delivering energy into the reaction vial are contemplated, including thermoelectric heating or cooling units, microwaves, heat lamps or laser light. The vessel 22 and vial 16 move up under control of a motion controller 162 which controls a vertical actuator 164 and a horizontal actuator 166 to seal to an interface on a stopper 152, 154, 156 or down to clear any tubing or wiring prior to lateral motion. Lateral motion aligns the vial 16 beneath one of at least 2 different stoppers 152, 154, 156 with fluidic interfaces. In a particular embodiment shown in FIGS. 13-17 the PRM has one axis of lateral motion with 3 positions. The fluidic interfaces provide (i) a sealed surface (for sealed reactions) such as shown in FIG. 17, (ii) tubing 158 for adding reagents such as shown in FIG. 14, (iii) tubing 158 for evaporating solvents, and (iv) tubing 158 and dip tube 124 for transferring product out of the vessel through the output stopper 156 (see FIGS. 14-16). Port and tubing connections and stopper order can be configured for the particular needs of a synthesis. FIG. 14 depicts a typical arrangement: stopper 142 is used for adding reagents and performing solvent evaporations, stopper 152 is used for sealed reactions, and stopper 156 is used for product transfer out of the reaction vial 16.

Sealing is achieved by pushing the top rim of the vial 16 up against a flat elastomeric or plastic gasket layer, typically an insert material such as Viton®, silicone, or Viton® with a protective Teflon® (FEP) film for particularly harsh reagents on the stoppers 152, 154, 156. For example, the stopper can be constructed from rigid materials (e.g. plastics such as PEEK or Ultem, or metal) with a gasket layer on the bottom surface. The stoppers are installed securely so they remain in place while the vial is pushed up against the bottom surface. In a specific embodiment of the present invention, pneumatic force is used to control the sealing force accurately, despite mechanical variations in the vial dimensions, gasket thicknesses, or mechanical tolerances of the system itself. A stepper motor is used to move the vial among the 3 fluid interface positions aligned along a single axis. In addition to a linear array, other configurations of fluid interfaces are contemplated, including two-dimensional arrays, or circular arrays (e.g. carousels). Configurations with 2, 3 or more than 3 fluid interface positions are also envisioned, depending on the needs of the chemical process. Means of positioning other than pneumatic actuation or stepper motors are possible, including hydraulics, servo motors, etc. FIGS. 14-17 illustrate the sequence of motions as the reaction vial 16 is moved from fluidic interface 154 in position 1 to the fluidic interface 152 in position 2.

The robotic system also includes several additional controls: (i) motion controller 162 for robotic motion of vial 16; (ii) valves 70 to control one or more ports of the fluid interface which is easier to vent (to permit filling of reaction vial 16 with reagents) or connected to vacuum (for evaporation), (iii) stir bar actuator (not shown), (iv) valves 70 to connect differential pressure to transfer fluid out of the vial 16 (positive pressure or vacuum).

As described above, a specific embodiment of the PRM 150 utilizes robotic control through three stations to facilitate functions required for a chemical reaction. The core component of the PRM 150 is a traditional v-shaped vial or vessel 16 in which all of the radiochemistry processes take place. The vial 16 is placed inside of an aluminum heater 22 fixed to a rigid platform. The platform can move vertically using two pneumatically actuated cylinders 164 (SMC, Japan). A stepper motor (Anaheim Automation, CA) drives the platform horizontally (the horizontal actuator 166). The reactor platform and cylinders are fixed to a seat that moves with the lead screw connected to the motor. The horizontal motion moves the vial 16 between three stations. Each station is defined by a lid or stopper 152, 154, 156 that the reactor platform seals against, using the vertical motion of the pneumatic cylinders. The stopper design is dependent on the function required at each station. For performing sealed reactions, a stopper 152 comprising an FEP protective sheet is placed on a viton gasket to provide a chemically inert surface at volatile conditions. At other stations, stoppers 154, 156 provide inlets and outlets for the addition or removal of reagents, the supply of heated air, or the removal of vapor through a vacuum line.

One of the advantages of the PRM 150 over traditional oil-bath/vial reactions is the ability to achieve high pressures and temperatures by incorporating pneumatic cylinders to seal the vial against a chemically inert gasket. The PRM 150 utilizes an actively heated and cooled aluminum reactor block (the heater 22). Miniature heater cartridges (Watlow, Mo.) are fixed within the reactor block. Vents machined into the aluminum are supplied with regulated air pressure, cooled gas, or cooled liquid for active cooling. Temperature control is accomplished through a k-type thermocouple embedded in the reactor, which provides feedback to the controller 160 (Omega, Conn.). Calibration of temperature within the vial 16 was accomplished by placing a second thermocouple through a brass Swagelok fitting embedded in the gasket covered lid used for sealing. Temperature profiles were then acquired to determine the lag time of the vial 16 temperature compared to the thermocouple measurement embedded in the reactor. Two tests were performed on the gasket seal: increasing pressure by direct injection of compressed air (up to 200 psi) into the reaction vial, and internal pressure generation by superheating volatile organic solvents (acetonitrile or dichloroethane up to 200° C.) in the sealed reaction position. The tests were each performed at least 3 times, for 1 hour. Vial contents were measured before and after tests to determine any evaporation losses due to poor sealing.

Figure 11:
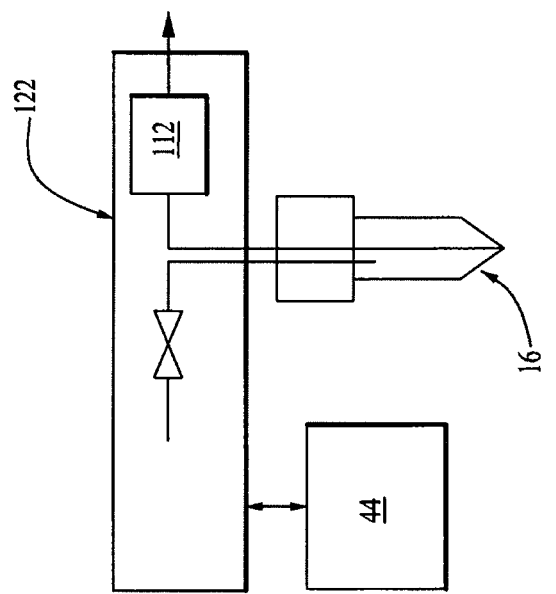
FIGS. 10 and 11 are schematic of a representations of two embodiments of liquid transfer subsystems.
Figure 10:
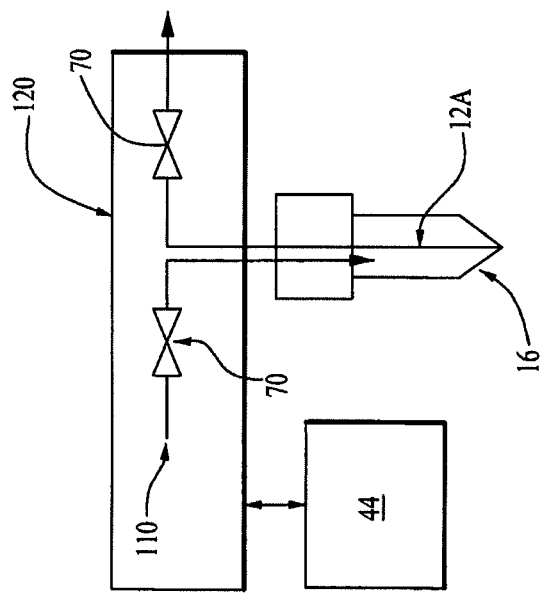

FIGS. 10 and 11 are a schematic representation of liquid transfer subsystems 120 that moves product solution from the reaction vial 16 to the next module in the system (for example, a purification module). In one embodiment, shown in FIG. 10, a valve 70 pressurizes the headspace above the liquid and forces it into the dip tube connected to the next module in the system. In another embodiment, shown in FIG. 11, a pump 112 draws the solution out of the reaction vial 16. A vent permits air or inert gas to replace the liquid removed from the vial.

Microwave Reaction Module (MRM)

Figure 18:
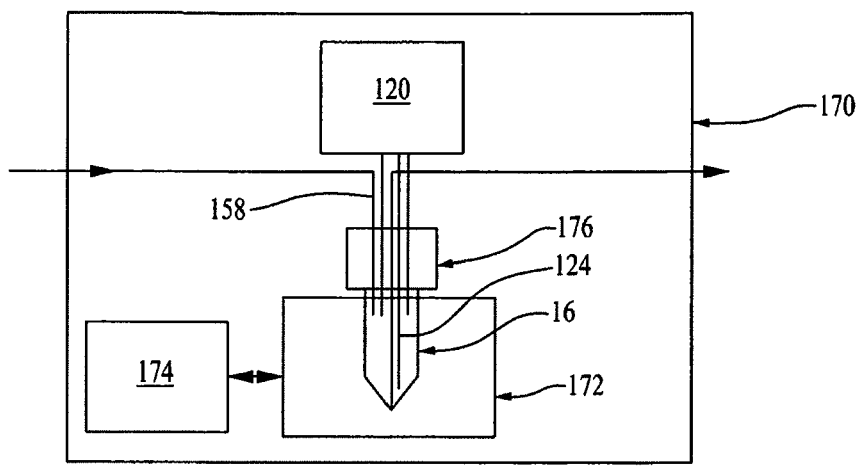
FIG. 18 is a schematic representation of a microwave reaction module.

The MRM 170 shown in FIG. 18 consists of a microwave cavity 172 (such as a miniature cavity provided by CEM Corporation) that accepts a reaction vial 16. The cavity 172 has a control unit 174 that may include microwave power control, temperature control, cooling gas, temperature monitoring, and stir bar control.

The vial 16 has a multi-port adapter interface ("lid") 176 (for example, PEEK with Kalrez® or Viton® seal) with ports for tubing 158 and tubing connector. These ports can be connected to other modules, e.g. a reagent delivery module 100, a vacuum evaporation system (described below), the pressurized transfer system as described above, and the downstream module (e.g. purification module 130) from the dip tube 124. In addition to control of the microwave reaction itself, this module has auxillary controls 120, for example, for venting the vial as reagents are added, applying vacuum and/or a gas stream for evaporations, or applying different pressure to transfer product out of the reactor. The MRM has an input port for the reaction product of the previous module (if one exists), and an output port connected to the next module in the system (if one exists).

No commercial synthesizer contains a microwave energy delivery system. This module permits this capability to be integrated into any process (e.g. existing manual setup, or a modified automated system). Furthermore, this platform permits comparison of a microwave reactor with a conventional reactor without changing any other parts of the system. One skilled in the art will recognize that delivering microwave energy to the reactants in the vial 16 in place of conventional heating may vary the reaction parameters, particularly reaction time, and the ratio of end products as the microwave energy couples directly with the reactants and may not in fact directly heat the solvents in which the reactants are delivered to the vial 16.

External QC/Analysis/Purification Interface Module (APIM)

Figure 19:
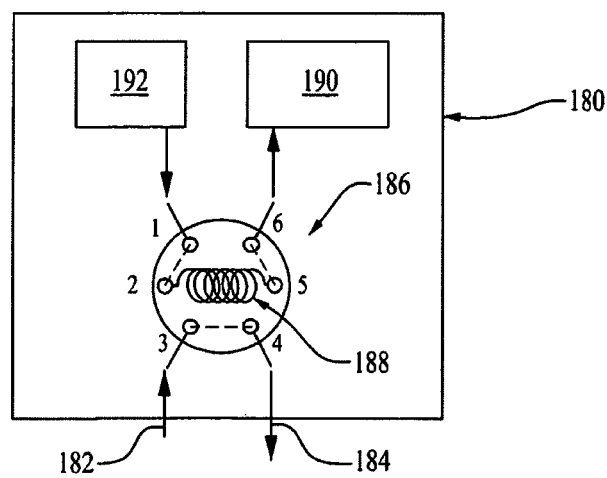
FIG. 19 is a schematic representation of an analytical QC or purification system interface module.

The APIM 180 shown schematically in FIG. 19, provides an interface between the modular platform and an external system for QC, analysis of reaction mixtures, or purification (e.g. HPLC).

The APIM has an input 182 for the reaction mixture and an output 184 connected to the next module in the system (if one exists). In one embodiment, this module uses a rotary injection valve 186 to capture a certain volume in an injection loop 188 (a small volume for analytical/sampling purposes, or the entire volume for preparative purification purposes). The valve 186 is switched from input to output to inject this volume into the external system. Any remaining volume (above the injection loop volume) is passed through to the next module in sequence. The module includes a sample analyzer 190 and a pump 192 for moving the withdrawn sample. There are many types of QC, analysis, and purifications that can be performed. For radio-HPLC, the pump 192 could be an HPLC pump and the sample analyzer 190 could be an HPLC column and detector system. For radio-TLC, NMR, GC-MS or other analytical systems, the pump 192 could simply be pressurized gas to push the injection loop volume into a collection vial followed by manual transfer to the instrument. Full integration with an automated injection system is also contemplated.

This sample collection and transfer function of this module can be implemented in many ways, e.g. with solenoid valves, or a microfluidic chip if connected to a relatively low-pressure QC/analysis/purification system.

Aliquotting Module (AM)

Dividing a product into multiple doses or to perform reaction development often required splitting a radioactive sample into N equal (or non-equal) volumes for further processing.

The AM 200, shown in FIG. 20 accepts a sample or stream and divides it among a programmable set of outlets 202. In one embodiment, a multi-port selection valve 204 is used. The volume directed to the selected output is metered using a metering pump 206 (e.g. piezo-based micro-pump, syringe pump, etc.), or by repetitive filling and flushing of a fixed-volume injection loop. Both approaches can be adapted to provide the capability to deliver a distinct (programmable) volume to each output.

Alternatively a microfluidic implementation of this module that will have integrated valves to eliminate deadvolumes and reduce loss and carryover can be used.

F-18 Drying Module

The drying module 210 shown in FIG. 21 performs drying and phase transfer of [$^{18}$F] fluoride ion from its original form in dilute $^{18}$O-water from the cyclotron into a mixture of acetonitrile (or other dry, organic solvent) with K.2.2.2 (Kryptofix) a phase transfer agent, and $K_2CO_3$. Other phase transfer agents could alternatively be used. The module has an input for the aqueous [$^{18}$F]fluoride solution and an output for the dried complex in organic solvent.

In one embodiment, the module uses an evaporative process, first evaporating water, then azeotropically removing residual water by additions and evaporations of dry acetonitrile. Finally, the [$^{18}$F]fluoride is formulated into the final solvent and delivered to the next module. In one embodiment, evaporation is achieved by heating the vial and additionally injecting a stream of heated gas and applying vacuum. The auxiliary controller that performs these functions has also been described above in the context of the pressurized reaction module, microwave reaction module, etc. and could be considered a distinct module. Typical components are a temperature controller 212 connected to a gas heater 214 as well as a vacuum pump 216, the operation of each controlled by a module controller 218. Methods contemplated of heating the vial content include the use of a heating block, the use of microwave energy, etc.

Alternatively, microfluidic replacements for this module based on microfluidic evaporation or electrochemical trapping and release techniques can be used.

More generally, the hardware of this module can be used as a solvent-exchange module (when solvent must be replaced with another solvent during the synthesis), or simply an evaporation module.

Concentration Module (CM)

The drying module 210 can also function to concentrate the product sample. This module has an input for the solution to be concentrated, and an output for the concentrated solution. After purifications, such as by solid-phase extraction (SPE) or HPLC, the volume of the sample may be increased to several mL or 10's of mL. This volume is too large to perform later chemical reaction steps. Thus, the volume must first be reduced. In some cases, the final product (at the end of the synthesis) must be reduced in volume to meet injection requirements for the patient or research animal.

In one embodiment, the CM such as shown in FIG. 21 uses vacuum-assisted evaporation to remove solvent to concentrate a sample. The sample is loaded into a vial 16 that functions as an evaporation reservoir. It is then heated (temperature determined according to chemistry and stability of solute) and vacuum applied to remove solvent until the desired degree of concentration has been achieved.

Alternatively a microfluidic version of this module, where the solvent is evaporated through a gas-permeable membrane, optimizing the tradeoff between large surface area (for fast evaporation) and small surface area (for low loss of reaction mixture).

Radiation Counting Module (RCM)

Figure 23:
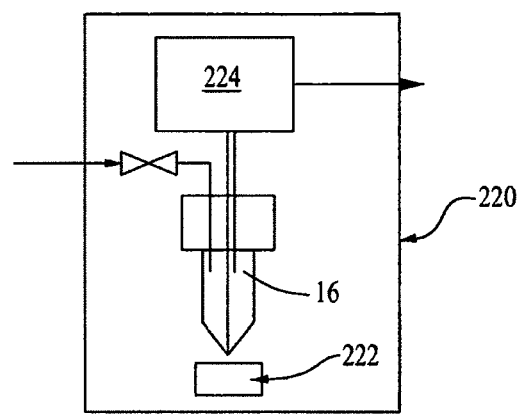
Figure 24:
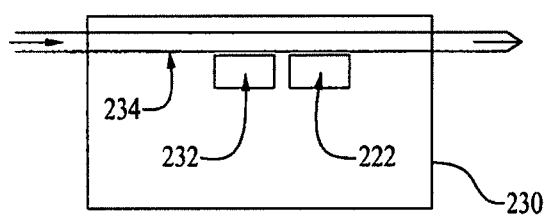

The RCM measures the radioactivity of a liquid sample. Two implementation examples are shown in FIGS. 23 and 24. This module has an inlet to accept a sample to be measured, one outlet to transfer this sample to the next module in the system and a radiation detector to measure the radioactivity of the sample.

In a first embodiment 220, the sample is loaded into a vial 16 in proximity to a calibrated radiation sensors 222 by a liquid transfer system 224. A measurement is made and the sample is transferred out.

Figure 22:
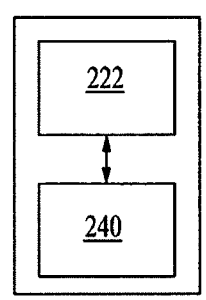
FIGS. 22, 23 and 24 are schematic representations of embodiments of a radiation counting module.

In a second embodiment 230, the sample flows in a channel 234 through the system. A flow rate sensor 232 in combination with a calibrated radiation sensor 222 is monitored to integrate the total radioactivity passing the detection point and arrive at the total radioactivity. FIG. 22 is a schematic of the radiation sensor with controller and readout 240.

There are a wide variety of methods than can be used to measure the radioactivity, including but not limited to PMTs and solid-state sensors.

Capillary Reactor Module (CRM)

Figure 25:
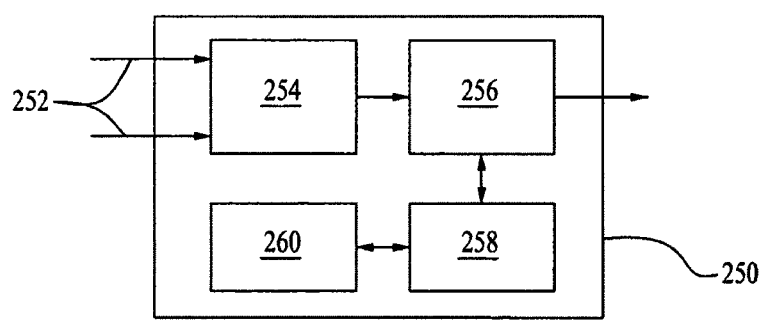
FIG. 25 is a schematic representation of a capillary or microfluidic reaction module.

The CRM 250 shown in FIG. 25 performs reactions in capillaries or microchannels. Two or more liquid streams 252 are pumped into a mixer 254 and then fed into capillary tubes or channels in a microfluidic chip 256 heated by an energy transfer subsystem 258, possibly connected to a controller 260. The streams can be pumped at different rates, or different ratios to achieve different residence times through the capillary.

In one embodiment, the pumps are syringe pumps that first load the two liquid samples into injection loops and then pump these samples at the desired flow rates into the capillary tubes or microchannels 256.

Commercial radiosynthesizers based on capillary and chip reactions exist. However, this subsystem is envisioned as a standalone reaction module that can be integrated into a multi-module radiochemical synthesis platform. It presents the same interface as the PRM or MRM (inlet for product of previous module, inlet for new reagents, and outlet to the next module) such that these three reactor types are essentially interchangeable.

Figure 26:
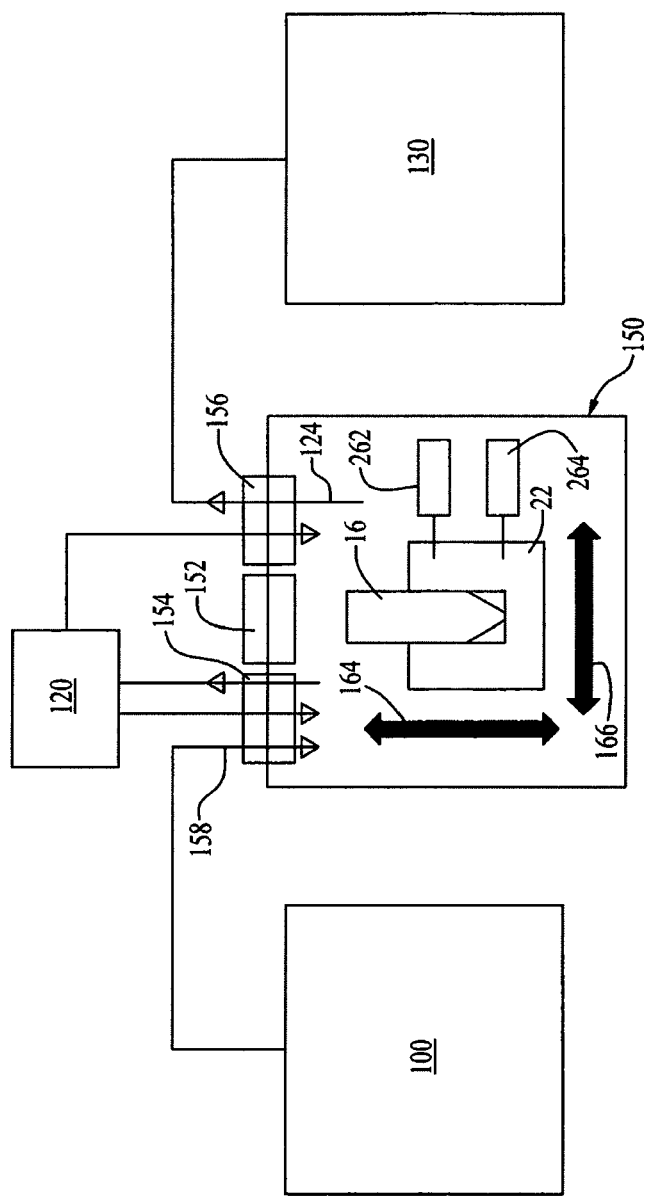
FIG. 26 is a schematic representation of a multiple module reaction system.

FIG. 26 shows a schematic representation of a multi-module reaction system including a reaction module (PRM) 150, cartridge purification module (CPM) 130, reagent delivery module (RDM) 100 and an auxiliary reaction subsystem 120 responsible for venting during reagent addition, evaporation, and product transfer after reaction. The reaction vial 16 is mounted within a heat transfer block including heating controller 262 and a cooling controller 264 such as used in the following examples.

Example 1

[$^{18}$F]FAC Synthesis Non-Robotic

To develop a process for the radiosynthesis of [$^{18}$F]FAC on the modular radiochemical synthesis system, steps are first optimized by performing manually with PRM modules as follows. "Manual" means that all the reagents were added directly into the reaction vial 16 manually (by hand) and only the PRM 150 is used to perform the reaction without using RDM 100 and CPM 130. Operations of the PRM were operated with remote-control units with touch-screen interfaces. The three PRM units are identified as #1, #2 and #3.

Fluorination using PRM #1

The first step of [$^{18}$F]FAC synthesis is critical to the final radiochemical yield. The procedure is as follows:

- Load F-18 solution into a vial containing the solution of $K_2CO_3$ and $K_{222}$ in MeCN: $H_2O$ (95:5)
- Measure activity
- Install vial into heat transfer block
- Use evaporation system to dry to get [K⊂K2.2.2][$^{18}$F]F
- Add precursor (tribenzoyl pentose triflate, ~10 mg) in MeCN (0.5 mL) into the reaction vial (RV)
- Seal RV by moving to position 2 (See FIG. 27). Heat RV to 165° C. for 15 min for radiofluorination
- Cool down RV below 60° C.
- Check the conversion yield using radio-HPLC (C-18 column, 1 mL/min, MeCN: $H_2O$ (70:30) as mobile phase, UV setting @ 254 nm) and radio-TLC ($SiO_2$, acetone: hexanes (30:70) as developing agent)
- Pass the reaction mixture through silica cartridge (pretreated with hexanes)
- Elute $^{18}$F-1 out using 4×1 mL of EtOAc into a collection vial
- Measure the activity of $^{18}$F-1 to obtain the radiochemical yield
- Check the radiochemical purity of $^{18}$F-1 using radio-HPLC and radio-TLC
- This procedure is repeated adjusting operating parameters (temperature, time) until a repeatable/reasonable yield was obtained.

Bromination and Cytosine Coupling Via PRM #2

These two steps involve two sensitive reagents, i.e. HBr and silylated precursor. The procedure is as follows:

- $^{18}$F-1 solution from the above procedure is added to RV of a second PRM;
- Evaporate EtOAc elution to dryness at 90° C. with hot air and under vacuum in Position 1 (See FIG. 28).
- Measure activity to determine if there is any activity loss due to evaporation
- Add 0.1 mL of HBr in acetic acid to RV, handling HBr within dry box
- Add 0.4 mL of dichloroethane into RV
- Seal RV (Position 2) and heat RV at 75° C. for 10 min for bromination
- Evaporate HBr/AcOH/dichloroethane at 75° C. to about half of the original volume
- Measure activity to determine if there is any activity loss due to evaporation
- Add 0.7 mL of toluene into RV
- Evaporate to dryness at 110° C. assisted with hot air and vacuum in Position 1
- Measure activity to determine if there is any activity loss due to evaporation
- Add 50 mg of silylated precursor in 1 mL of dichloroethane into RV
- Seal RV (Position 2) and heat RV to 160° C. for 30 min for coupling
- Cool down below 60° C.
- Check the coupling yield using radio-HPLC and radio-TLC
- Pass the reaction mixture through silica gel cartridge (pretreated with hexanes)
- Elute $^{18}$F-3 out using 5×1 ml of MeOH:$CH_2Cl_2$ (10:90) into a collection vial
- Measure the activity of $^{18}$F-3 to check the radiochemical yield
- Obtain the radiochemical purity of $^{18}$F-3 using radio-HPLC and radio-TLC
- This procedure is repeated, tuning reaction conditions and observing outcomes until a process for repeatable/reasonable yield is achieved.

Deprotection using PRM #3

The deprotection step also involves a sensitive reagent, sodium methoxide solution.

- Add $^{18}$F-3 solution prepared above to RV of PRM #3
- Evaporate elution solution (MeOH:$CH_2Cl_2$ (10:90)) to complete dryness at 100° C. assisted with hot air and vacuum in Position 1
- Measure activity (to determine if there is any activity loss due to evaporation)
- Add 0.5 mL of 0.5M sodium methoxide solution into RV
- Seal RV (Position 2) and heat to 100° C. for 5 min
- Cool down below 60° C.
- Add 0.25 mL of 1N HCl into RV
- Check the reaction yield using radio-HPLC (C-18 column, 1 mL/min, EtOH: 50 mM $NH_4OAc$ in water (10:90) as mobile phase, UV setting @ 254 nm) and radio-TLC ($SiO_2$, $CH_2Cl_2$: MeOH (85:15) as a developing agent) (See FIG. 29)
- Evaporate MeOH out of the solution at 100° C. assisted with hot air and under vacuum in Position 1
- Measure activity (to determine if there is any activity loss due to evaporation)
- Add 3 mL of HPLC mobile phase into RV to dilute the residue
- Inject into preparative HPLC and collect fractions
- Measure the activity of $^{18}$F-4 to obtain the radiochemical yield
- Check the radiochemical purity of $^{18}$F-4 using radio-HPLC and radio-TLC
- This procedure is repeated and reaction parameters adjusted until a repeatable/reasonable yield is obtained.

Example 2

Synthesis of [$^{18}$F]FAC in the Integrated System, Including RDM, PRM and CPM

Figure 30:
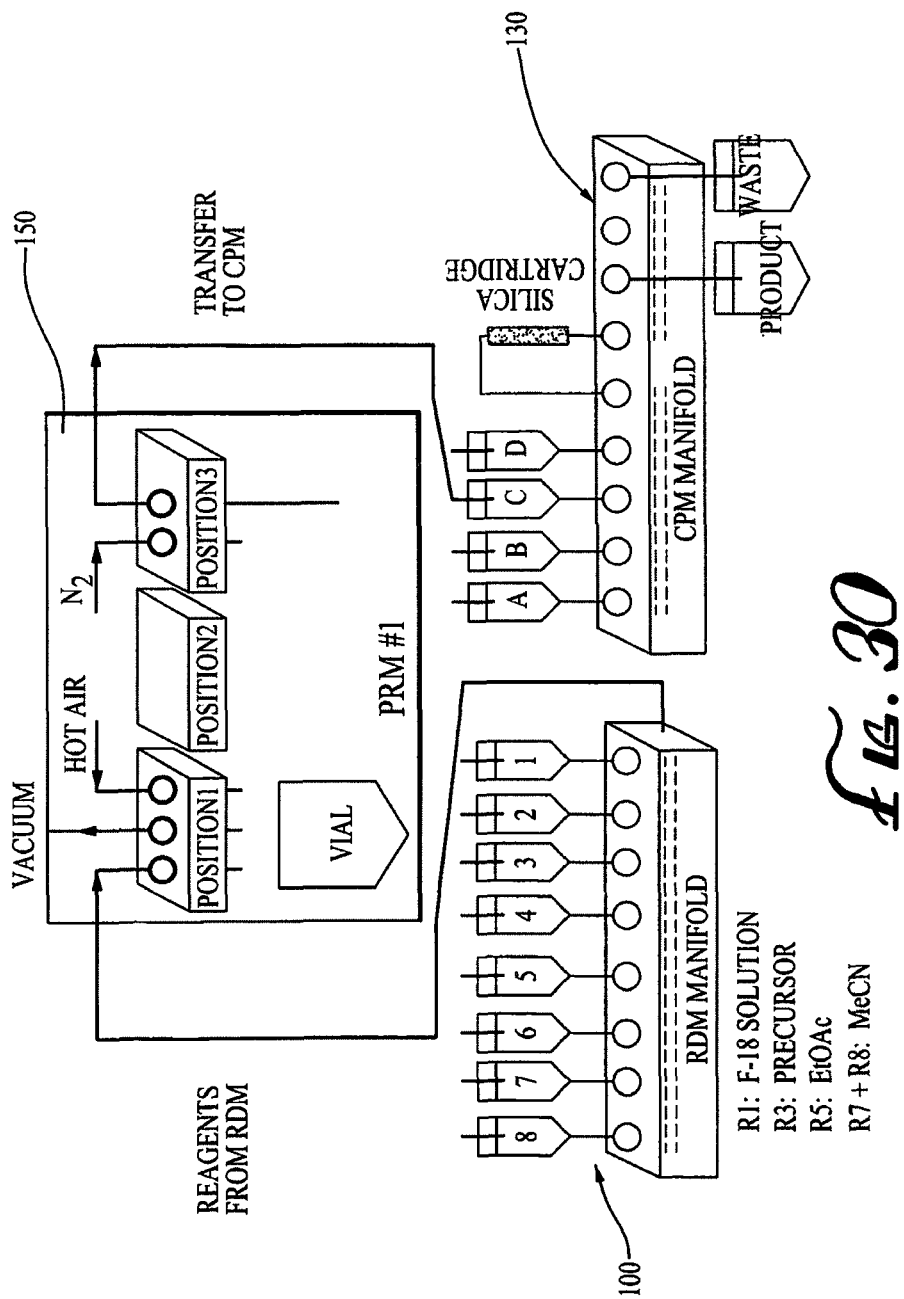
FIG. 30 is a schematic representation of the fluorination step, using a first modular system incorporating features of the invention, in the robotic synthesis of [$^{18}$F] FAC.
Figure 31:
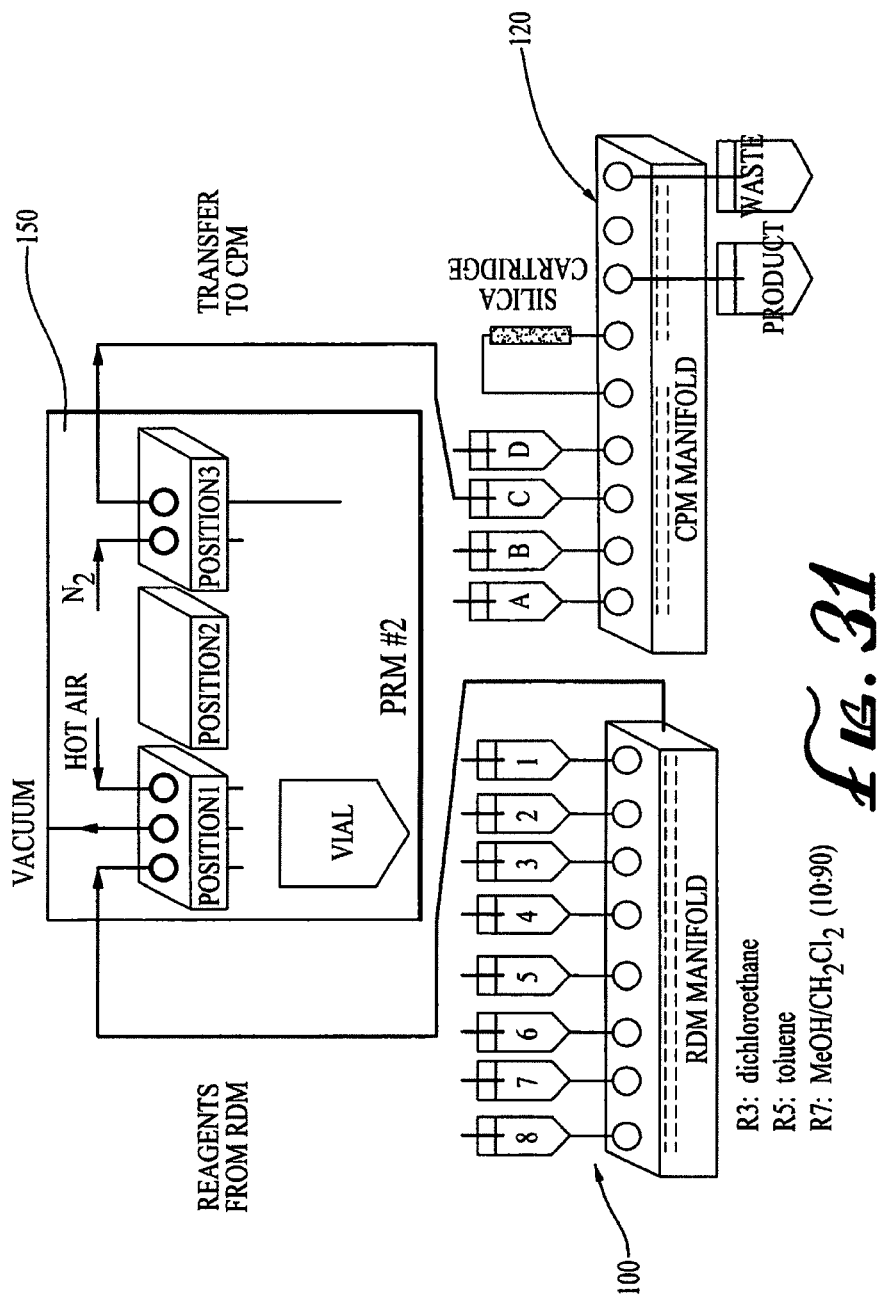
FIG. 31 is a schematic representation of the bromination and cytosine coupling step using a second modular system incorporating features of the invention, in the robotic synthesis of [$^{18}$F] FAC.
Figures 32, 33:
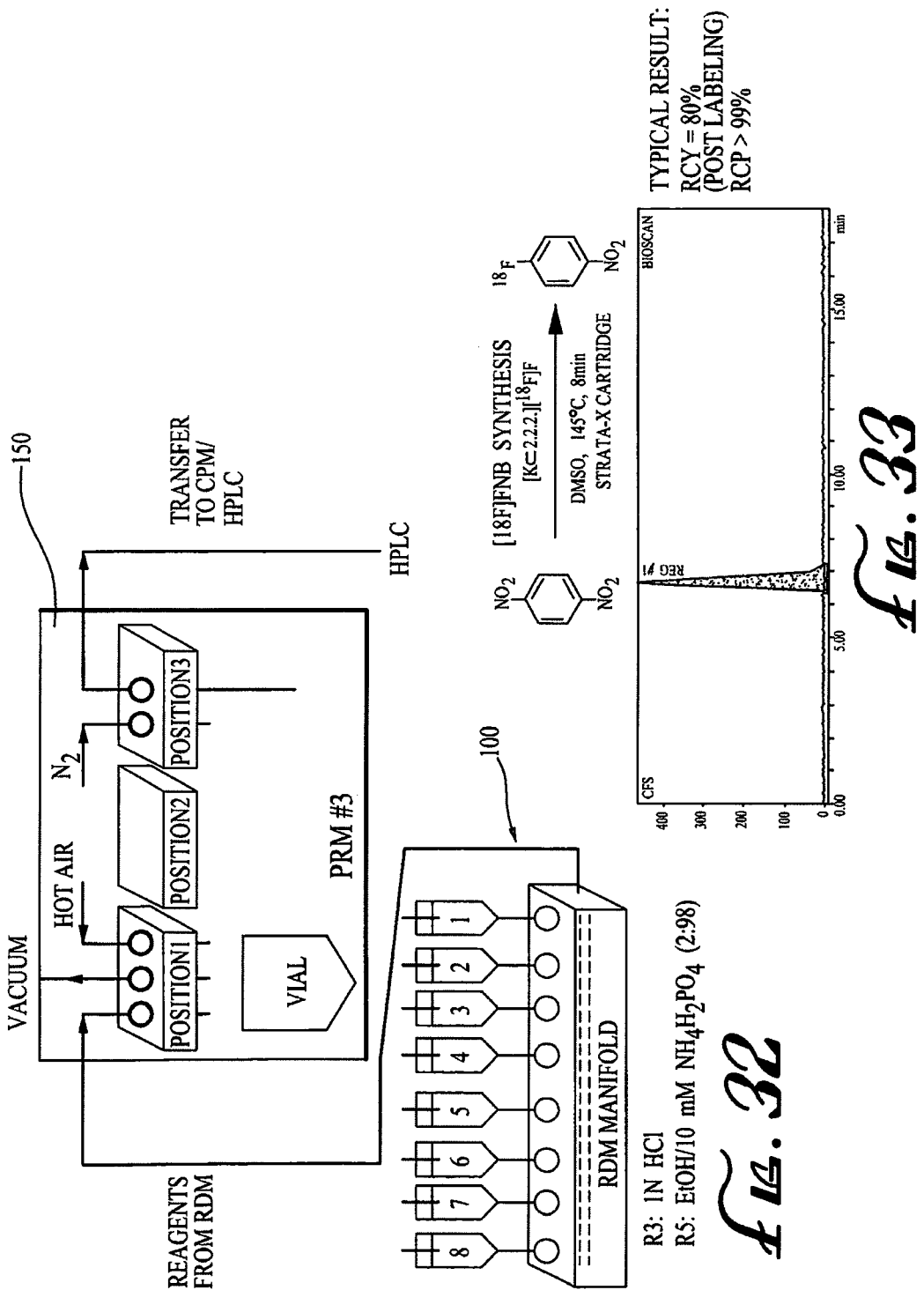
FIG. 32 is a schematic representation of the deprotection step using a third modular system incorporating features of the invention, in the robotic synthesis of [$^{18}$F] FAC.
FIG. 33 is a radio-HPLC spectrum of [$^{18}$F] FNB produced using a modular system incorporating features of the invention.

"The integrated ARC-P system" includes three sequential sets of RDM 100, PRM 150 and CPM 130 as shown in FIGS. 30-32. All of the reagents for reaction and separation were added into the reaction vial (RV) 16 by passing through the RDM 100. The PRM 150 is used to perform evaporations and heating, and the CPM 130 is used for the cartridge purification. The preparation of [$^{18}$F] FAC follows the reaction scheme and the description given below

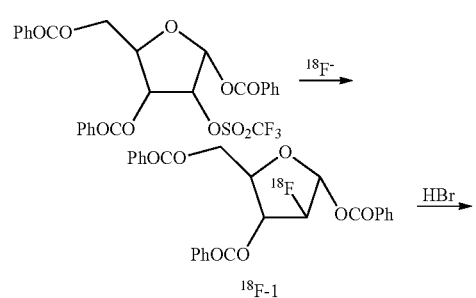

-continued

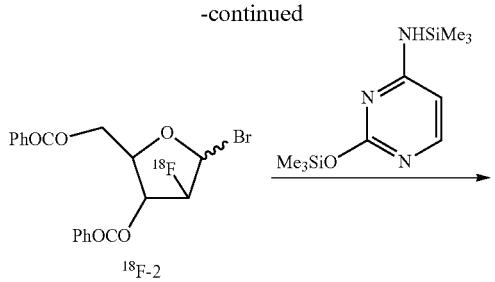

¹⁸F-2

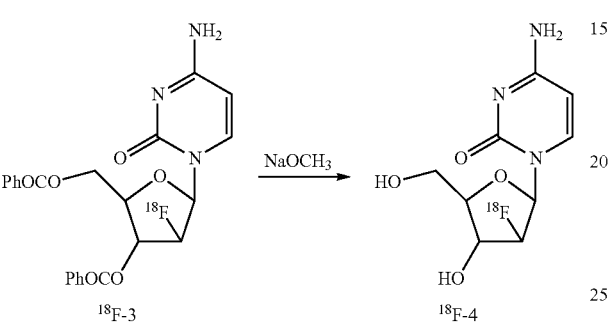

¹⁸F-3          ¹⁸F-4

Fluorination (Referring to FIG. 30)
Transfer aqueous F-18 solution containing $K_{222}/K_2CO_3/$ MeCN from chamber 1 (R1) in the RDM manifold into the reaction vial (RV) to prepare $[K \subset K2.2.2][^{18}F]F$
Heat RV to 110° C. for 1 min assisted with hot air and vacuum in Position 1 (1st F-18 drying)
Cool down below 60° C.
Transfer 1 mL of MeCN from R7 into RV
Heat RV to 110° C. for 1 min assisted with hot air and vacuum in Position 1 (2nd drying)
Cool down below 60° C.
Transfer 1 mL of MeCN from R8 into RV (3rd
Heat RV to 110° C. for 3 min assisted with hot air and vacuum in Position 1 drying)
Heat RV at 110° C. for additional 3 min with vacuum only in Position 1 (final drying step)
Transfer the precursor (tribenzoyl pentose triflates, 10 mg) in 0.5 mL of MeCN from R3 into RV
Seal and heat RV to 165° C. for 15 min in Position 2 for radiofluorination
Cool down below 60° C.
Check the conversion yield using radio-HPLC (C-18 column, 1 mL/min, MeCN:H₂O (70:30) as mobile phase, UV setting @ 254 nm) and radio-TLC (SiO₂, acetone:hexanes (30:70) as developing agent)
Pass the reaction mixture through silica gel cartridge (pretreated with hexanes)
Elute ¹⁸F-1 out using 4×1 mL of EtOAc into RV #2
Measure the activity of ¹⁸F-1 to obtain the radiochemical yield
Check the radiochemical purity of ¹⁸F-1 using radio-HPLC and radio-TLC
Bromination and Cytosine Coupling (FIG. 31)
Transfer ¹⁸F-1 solution to RV of PRM #2
Evaporate eluate to dryness at 90° C. assisted with hot air and vacuum in Position 1
Measure activity to determine if there is any activity loss due to evaporation.
Add 0.1 mL of HBr in acetic acid to RV #2

Transfer 0.4 mL of dichloroethane from R3 into RV #2
Seal and heat RV to 75° C. for 10 min in Position 2 for bromination
Evaporate HBr/AcOH/dichloroethane at 75° C. to about half of the original volume
Measure activity to determine if there is any activity loss due to evaporation
Transfer 0.7 mL of toluene from R5 into RV
Evaporate to dryness at 115° C. (110° C. inside the vial) with hot air of 130° C. and under vacuum (−10~15 in. Hg) in Position 1
Measure activity to determine if there is any activity loss due to evaporation
Add 50 mg of silylated precursor in 1 ml of dichloroethane into RV by passing either through a tubing outside the hotcell remotely, or via RDM
Seal and heat RV to 160° C. for 30 min in Position 2 for coupling
Cool down below 60° C.
Check the coupling yield using radio-HPLC and radio-TLC
Pass the reaction mixture through silica cartridge pretreated with hexanes
Elute ¹⁸F-3 out using 5×1 mL of MeOH: CH₂Cl₂ (10:90) from R7 into a collection vial or RV #3
Measure the activity of ¹⁸F-3 to check the radiochemical yield
Check the radiochemical purity of ¹⁸F-3 using radio-HPLC and radio-TLC
Deprotection (FIG. 32)
Transfer ¹⁸F-3 solution to RV #3 in PRM #3; Evaporate elution solution (MeOH:CH₂Cl₂ (10:90)) to complete dryness at 100° C. assisted with hot air and vacuum in Position 1
Measure activity
Transfer 0.5 mL of 0.5M sodium methoxide solution into RV #3 by passing, either through a tubing outside the hotcell remotely, or via RDM
Heat to 100° C. for 5 min in Position 2
Cool down below 60° C.
Transfer 0.25 mL of 1N HCl from R3 into RV #3
Check the deprotection yield using radio-HPLC (C-18 column, 1 mL/min, EtOH: 50 mM NH₄OAc in water (10:90) as mobile phase, UV setting @ 254 nm) and radio-TLC (SiO₂, CHCl₃: MeOH (10:90) as developing agent)
Evaporate MeOH out of the solution at 100° C. assisted with hot air and vacuum in Position 1
Measure activity
Transfer 3 mL of HPLC mobile phase from R5 into RV #3 to dilute the residue
Inject solution in RV #3 into preparative HPLC and collect fractions
Measure the activity of ¹⁸F-4 to check the radiochemical yield
Check the radiochemical purity of ¹⁸F-4 using radio-HPLC and radio-TLC.

Example 3

Preparation of D-2'-deoxy-2'-[$^{18}$F]fluoro-β-D-arabinofuranosylcytosine (D-[$^{18}$F]FAC)

The preparation of D[$^{18}$F] FAC follows the reaction scheme and the description given below:

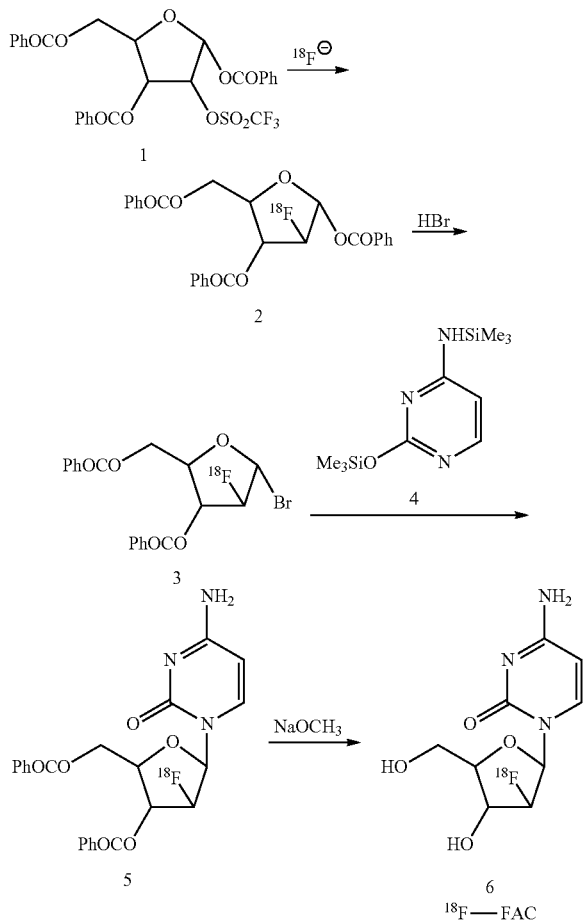

2-O-[(Trifluoromethyl)sulfonyl]-1,3,5-tri-O-benzoyl-α-D-ribofuranose (1) was prepared as reported in the literature (Tann, C. H., Brodfuehrer, P. R., Brundidge, S. P., Sapino, Jr. C., and Howell, H. G. "Fluorocarbohydrates in Synthesis. An Efficient Synthesis of 1-(2-Deoxy-2-fluoro-β-D-arabinofuranosyl)-5-iodouracil (β-FIAU) and 1-(2-Deoxy-2-fluoro-β-D-arabinofuranosyl)thymine (β-FMAU)". *J. Org. Chem.*, 50, pp 3644-3647(1985)) The synthesis of the $^{18}$F-fluoro analog 2 was carried out by a modification of the method reported by Mangner et al. (Mangner, T. J., Klecker, R. W., Anderson, L., and Shields, A. F. "Synthesis of 2'-deoxy-2' [$^{18}$F]fluoro-β-D-arabinofuranosyl nucleosides, [$^{18}$F]FAU, [$^{18}$F]FMAU, [$^{18}$F]FBAU and [$^{18}$F]FIAU, as potential PET agents for imaging cellular proliferation", *Nuc. Med. Biol.*, 50, pp 215-224 (2003).

The radiosynthesis was carried out using three of the robotic reaction modules of FIGS. 1-4. No-carrier-added [$^{18}$F]fluoride ion was produced by 11 MeV proton bombardment of 98% enriched [$^{18}$O]water in a silver target body using a RDS-112 cyclotron. The aqueous [$^{18}$F]fluoride ion was treated with a solution of K$_2$CO$_3$ (1 mg) and Kryptofix 2.2.2 (10 mg) dissolved in water (0.04 mL) and acetonitrile (0.75 mL) mixture. The solution was evaporated at 115° C. with a stream of nitrogen gas. The residue was dried by the azeotropic distillation with acetonitrile (3×0.5 mL). A solution of the triflate 1 (10 mg) in 0.7 mL of acetonitrile was added to the dry residue and the reaction mixture was heated at 165° C. for 15 min in a sealed vessel. The solution was cooled to room temperature and passed through a small cartridge of silica gel. The product was eluted from the cartridge with 5 mL of ethyl acetate. The ethyl acetate solution was evaporated to dryness and 0.1 mL of a solution of 30% HBr in acetic acid was added followed by 0.4 mL of dichloroethane. This new reaction mixture was heated at 80° C. in a sealed vessel for 10 min and the solution was concentrated to ~50% of the initial volume. Toluene (0.7 mL) was then added and the solution was evaporated at 110° C. to give the bromo compound 3. A freshly prepared disilyl derivative of cytosine (4, 35 mg) was dissolved in 1 mL of dichloroethane and added to the bromo compound 3. The condensation reaction was carried out at 160° C. in a sealed vessel for 30 min. The reaction mixture was cooled to room temperature and then passed through a small column of silica gel. The product was eluted off the column using 5 mL of a solution mixture of 10% methanol and 90% dichloromethane. This solution was evaporated to dryness at 100° C. and then treated with 0.5 mL of a solution of 0.5 M sodium methoxide in methanol. The reaction mixture was heated at 100° C. for 5 min in a sealed vessel. The basic reaction mixture was neutralized with 0.25 mL of 1M HCl in water. This reaction mixture was diluted to a total volume of 3 mL with a mixture of 1% ethanol and 99% 10 mM ammonium dihydrogen phosphate in water and injected into a semi-preparative HPLC column (Phenomenex Gemini C-18 column; 25 cm×1 cm). The HPLC column was eluted with a solvent mixture of 1% ethanol and 99% 10 mM ammonium dihydrogen phosphate at a flow rate of 5.0 mL/min. The effluent from the HPLC column was monitored with a 254 nm UV detector followed by a gamma radioactive detector. The chemically and radiochemically pure D-[$^{18}$F] FAC that eluted off the column with a retention time of ~15 min was made isotonic with normal saline and sterilized by passing through a Millipore filter (0.22 μm) into a sterile multi-dose vial.

Chemical and Radiochemical Quality Control

Figure 37:
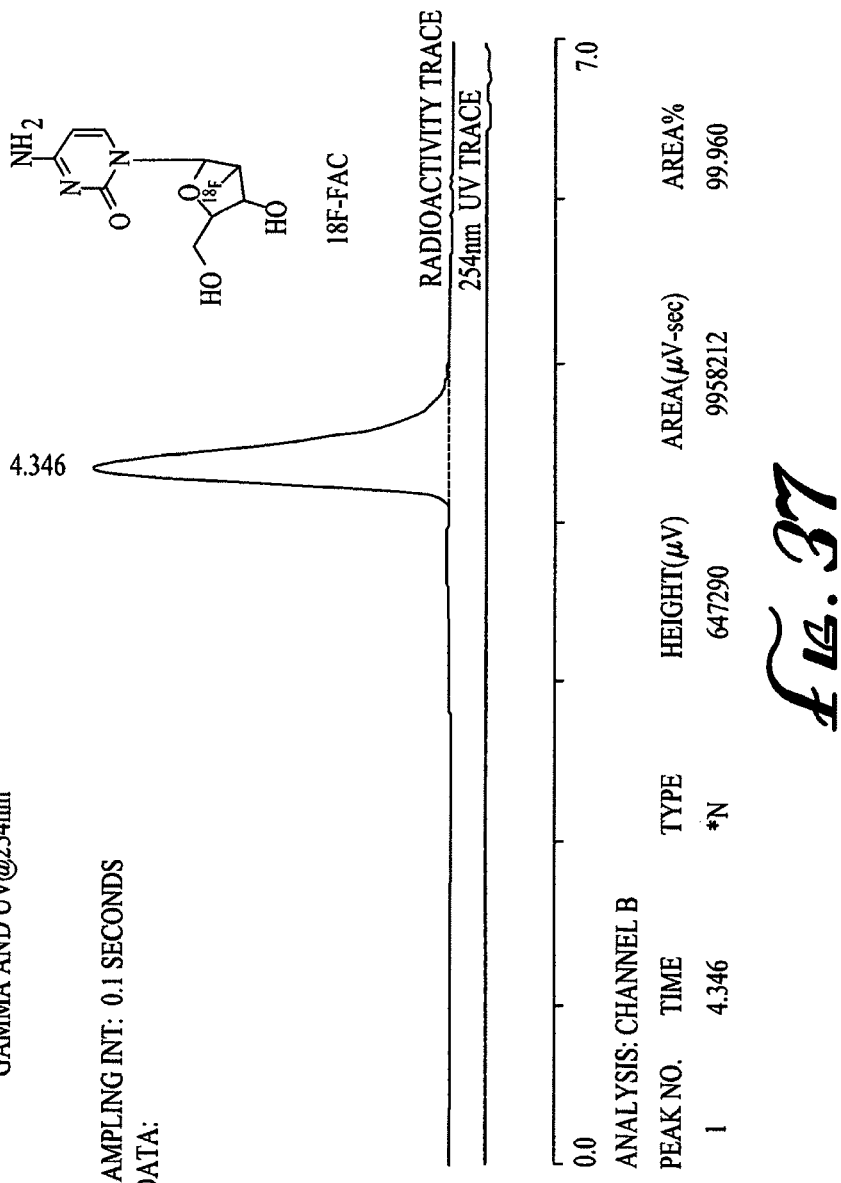
FIG. 37 is an HPLC chromatogram indicating the purity of D-[$^{18}$F] FAC.

The chemical and radiochemical purities of D-[$^{18}$F] FAC were determined by an analytical HPLC method using a Phenomenex Luna column (25 cm×0.46 cm, 5μ particle size). The column was eluted with 10% ethanol and 90% 50 mM ammonium acetate at a flow rate of 1.0 mL/min. The effluent from the HPLC column was passed through a UV detector (λ=254 nm) followed by a gamma radioactivity detector. The chemical and radiochemical purities of D-[$^{18}$F] FAC prepared as described above exceeded 99.9% as shown in the analytical HPLC chromatogram (see FIG. 37).

Analytical HPLC also was used to determine the specific activity of D-[$^{18}$F] FAC. A range of mass vs UV absorption at 254 nm wavelength for non-radiolabeled D-FAC was determined using the analytical HPLC method described above and the data set was used to construct a calibration graph. Using this calibration graph, the specific activity of D-[$^{18}$F] FAC was found to be 1000 Ci/mmol.

Radionuclide Analysis

A calibrated γ-ray spectrometer was used to establish the presence of the 511 keV annihilation radiation associated with the decay of $^{18}$F isotope.

Sterility and Pyrogenicity Tests

D-[$^{18}$F] FAC prepared as described above was tested for sterility using the standard thioglycollate medium procedure and found to be sterile.

The absence of pyrogens in the D-[$^{18}$F] FAC preparation was verified by the standard Limulus Amebocyte Lysate (LAL) test.

Example 4

Preparation of L-2'-Deoxy-2'-[$^{18}$F]fluoro-β-D-arabinofuranosylcytosine (L-[$^{18}$F] FAC)

The preparation of L-[$^{18}$F] FAC follows the reaction scheme and the description given below:

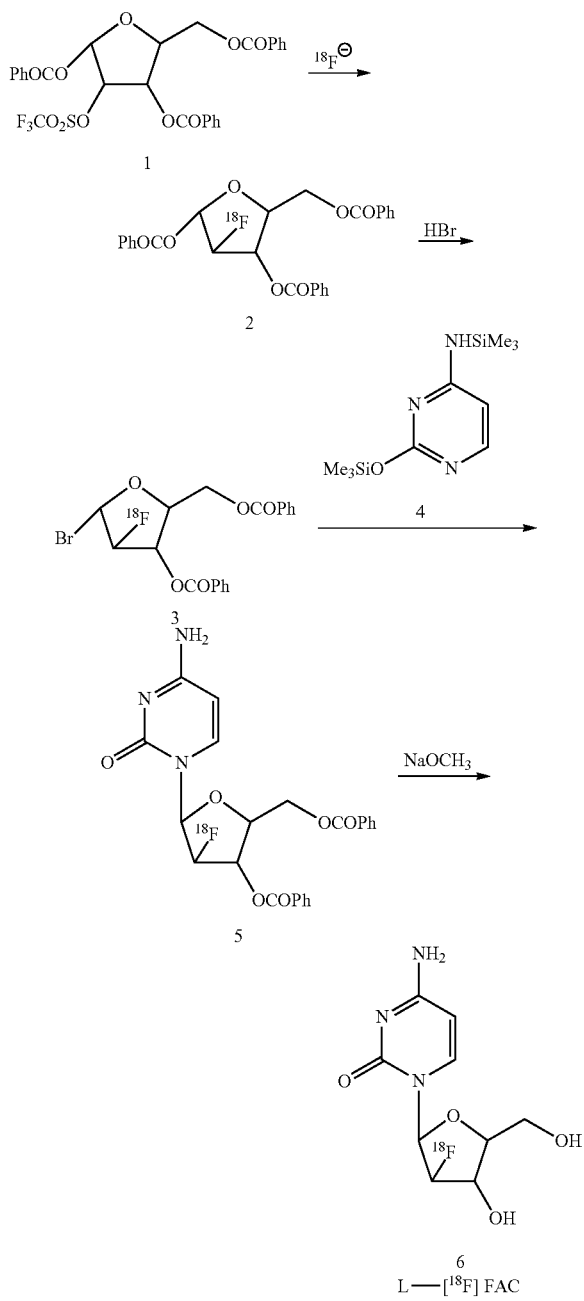

L-2-O-[(Trifluoromethyl)sulfonyl]-1,3,5-tri-O-benzoyl-α-D-ribofuranose (1) was prepared based on the procedure reported by Tann et al. for the corresponding D-isomer (Example 1).

The synthesis of the $^{18}$F-fluoro analog 2 was carried out by a modification of the above referenced method reported by Mangner et al. described for the corresponding D-isomer.

The radiosynthesis was carried out using three of the robotic reaction modules of FIGS. 1-4. No-carrier-added [$^{18}$F]fluoride ion was produced by 11 MeV proton bombardment of 98% enriched [$^{18}$O]water in a silver target body using a RDS-112 cyclotron. The aqueous [$^{18}$F]fluoride ion was treated with a solution of $K_2CO_3$ (1 mg) and Kryptofix 2.2.2 (10 mg) dissolved in water (0.04 mL) and acetonitrile (0.75 mL) mixture. The solution was evaporated at 115° C. with a stream of nitrogen gas. The residue was dried by the azeotropic distillation with acetonitrile (3×0.5 mL). To the dry residue, a solution of the triflate 1 (10 mg) in 0.7 mL of acetonitrile was added and the reaction mixture was heated at 165° C. for 15 min in a sealed vessel. The solution was cooled to room temperature and passed through a small cartridge of silica gel. The product was eluted from the cartridge with 5 mL of ethyl acetate. The ethyl acetate solution was evaporated to dryness and 0.1 mL of a solution of 30% HBr in acetic acid was added followed by 0.4 mL of dichloroethane. This new reaction mixture was heated at 80° C. in a sealed vessel for 10 min and the solution was concentrated to ~50% of the initial volume. Toluene (0.7 mL) was then added and the solution was evaporated at 110° C. to give the bromo compound 3. A freshly prepared disilyl derivative of cytosine (4, 35 mg) was dissolved in 1 mL of dichloroethane and added to the bromo compound 3. The condensation reaction was carried out at 160° C. in a sealed vessel for 30 min. The reaction mixture was cooled to room temperature and then passed through a small column of silica gel. The product was eluted off the column using 5 mL of a solution mixture of 10% methanol and 90% dichloromethane. This solution was evaporated to dryness at 100° C. and then treated with 0.5 mL of a solution of 0.5 M sodium methoxide in methanol. The reaction mixture was heated at 100° C. for 5 min in a sealed vessel. The basic reaction mixture was neutralized with 0.25 mL of 1M HCl in water. This reaction mixture was diluted to a total volume of 3 mL with a mixture of 1% ethanol and 99% 10 mM ammonium dihydrogen phosphate in water and injected into a semi-preparative HPLC column (Phenomenex Gemini C-18 column; 25 cm×1 cm). The HPLC column was eluted with a solvent mixture of 1% ethanol and 99% 10 mM ammonium dihydrogen phosphate at a flow rate of 5.0 mL/min. The effluent from the HPLC column was monitored with a 254 nm UV detector followed by a gamma radioactive detector. The chemically and radiochemically pure L-[$^{18}$F] FAC that eluted off the column with a retention time of ~15 min was made isotonic with normal saline and sterilized by passing through a Millipore filter (0.22 μm) into a sterile multi-dose vial.

Chemical and Radiochemical Quality Control

Figure 38:
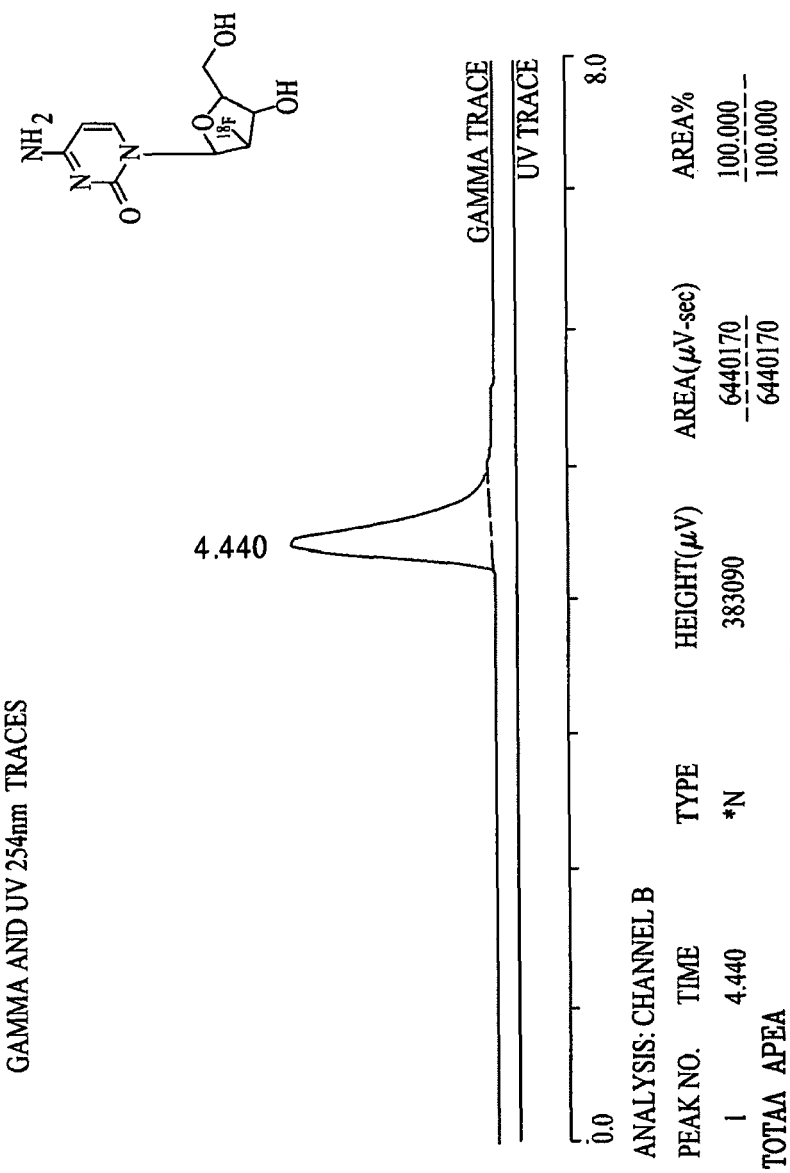
FIG. 38 is an HPLC chromatogram indicating the purity of L-[$^{18}$F] FAC.

The chemical and radiochemical purities of L-[$^{18}$F] FAC were determined by an analytical HPLC method using a Phenomenex Luna column (25 cm×0.46 cm, 5μ particle size). The column was eluted with 10% ethanol and 90% 50 mM ammonium acetate at a flow rate of 1.0 mL/min. The effluent from the HPLC column was passed through a UV detector (λ=254 nm) followed by a gamma radioactivity detector. The chemical and radiochemical purities of L-[$^{18}$F] FAC prepared as described above exceeded 99.9% as shown in the analytical HPLC chromatogram (FIG. 38).

Analytical HPLC also was used to determine the specific activity of L-[$^{18}$F] FAC. A range of mass vs UV absorption at 254 nm wavelength for non-radiolabeled L-FAC was determined using the analytical HPLC method described above and the data set was used to construct a calibration graph. Using this calibration graph, the specific activity of L-[$^{18}$F] FAC was found to be >1000 Ci/mmol.

Radionuclide Analysis

A calibrated γ-ray spectrometer was used to establish the presence of the 511 keV annihilation radiation associated with the decay of $^{18}$F isotope.

Sterility and Pyrogenicity Tests

L-[$^{18}$F] FAC prepared as described above was tested for sterility using the standard thioglycollate medium procedure and found to be sterile.

The absence of pyrogens in the L-[$^{18}$F] FAC preparation was verified by the standard Limulus Amebocyte Lysate (LAL) test.

Insert 0076

Example 5

Preparation of L-2'-Deoxy-2'-[$^{18}$F]fluoro-β-D-arabinofuranosyl-5-methylcytosine (L-[$^{18}$F] FMAC)

The preparation of L-[$^{18}$F] FMAC follows the reaction scheme and the description given below:

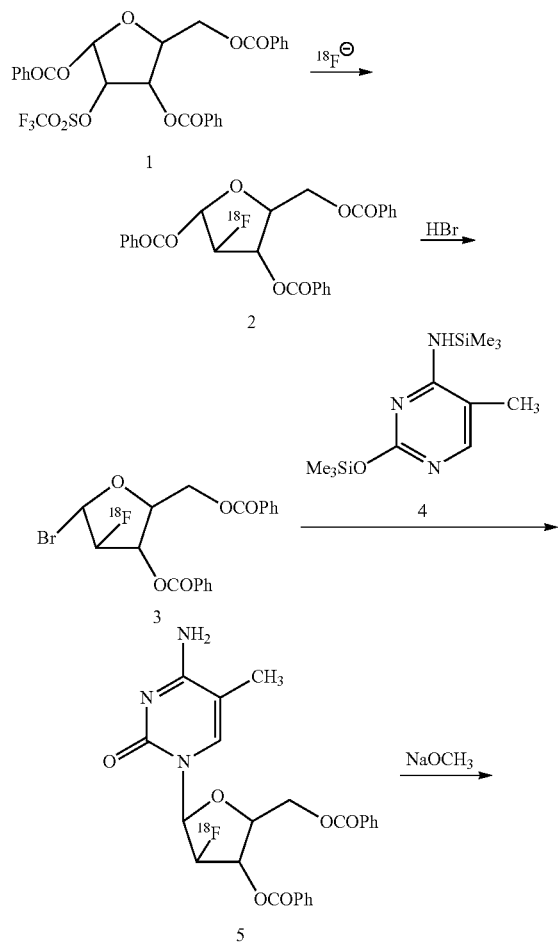

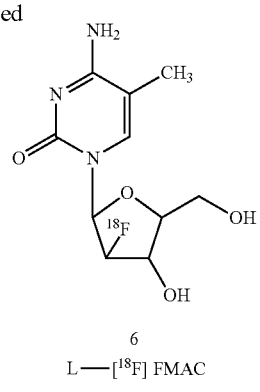

6
L—[$^{18}$F] FMAC

L-2-O-[(Trifluoromethyl)sulfonyl]-1,3,5-tri-O-benzoyl-α-D-ribofuranose (1) was prepared based on the procedure reported by Tann et al. for the corresponding D-isomer (referenced above). The synthesis of the $^{18}$F-fluoro analog 2 was also carried by a modification of the method reported by Mangner et al. The radiosynthesis was carried out using three of the robotic reaction modules of FIGS. 1-4. No-carrier-added [$^{18}$F]fluoride ion was produced by 11 MeV proton bombardment of 98% enriched [$^{18}$O]water in a silver target body using a RDS-112 cyclotron. The aqueous [$^{18}$F] fluoride ion was treated with a solution of $K_2CO_3$ (1 mg) and Kryptofix 2.2.2 (10 mg) dissolved in water (0.04 mL) and acetonitrile (0.75 mL) mixture. The solution was evaporated at 115° C. with a stream of nitrogen gas. The residue was dried by the azeotropic distillation with acetonitrile (3×0.5 mL). To the dry residue, a solution of the triflate 1 (10 mg) in 0.7 mL of acetonitrile was added and the reaction mixture was heated at 165° C. for 15 min in a sealed vessel. The solution was cooled to room temperature and passed through a small cartridge of silica gel. The product was eluted from the cartridge with 5 mL of ethyl acetate. The ethyl acetate solution was evaporated to dryness and 0.1 mL of a solution of 30% HBr in acetic acid was added followed by 0.4 mL of dichloroethane. This new reaction mixture was heated at 80° C. in a sealed vessel for 10 min and the solution was concentrated to ~50% of the initial volume. Toluene (0.7 mL) was then added and the solution was evaporated at 110° C. to give the bromo compound 3. A freshly prepared disilyl derivative of 5-methylcytosine (4, 35 mg) was dissolved in 1 mL of dichloroethane and added to the bromo compound 3. The condensation reaction was carried out at 160° C. in a sealed vessel for 30 min. The reaction mixture was cooled to room temperature and then passed through a small column of silica gel. The product was eluted off the column using 5 mL of a solution mixture of 10% methanol and 90% dichloromethane. This solution was evaporated to dryness at 100° C. and then treated with 0.5 mL of a solution of 0.5 M sodium methoxide in methanol. The reaction mixture was heated at 100° C. for 5 min in a sealed vessel. The basic reaction mixture was neutralized with 0.25 mL of 1M HCl in water. This reaction mixture was diluted to a total volume of 3 mL with a mixture of 1% ethanol and 99% 10 mM ammonium dihydrogen phosphate in water and injected into a semi-preparative HPLC column (Phenomenex Gemini C-18 column; 25 cm×1 cm). The HPLC column was eluted with a solvent mixture of 2% ethanol and 98% 10 mM ammonium dihydrogen phosphate at a flow rate of 5.0 mL/min. The effluent from the HPLC column was monitored with a 254 nm UV detector followed by a gamma radioactive detector. The chemically and radiochemically pure L-[$^{18}$F] FMAC that eluted off the column with a retention time of 15 min was made isotonic with normal saline and sterilized by passing through a Millipore filter (0.22 μm) into a sterile multi-dose vial.

Chemical and Radiochemical Quality Control

Figure 39:
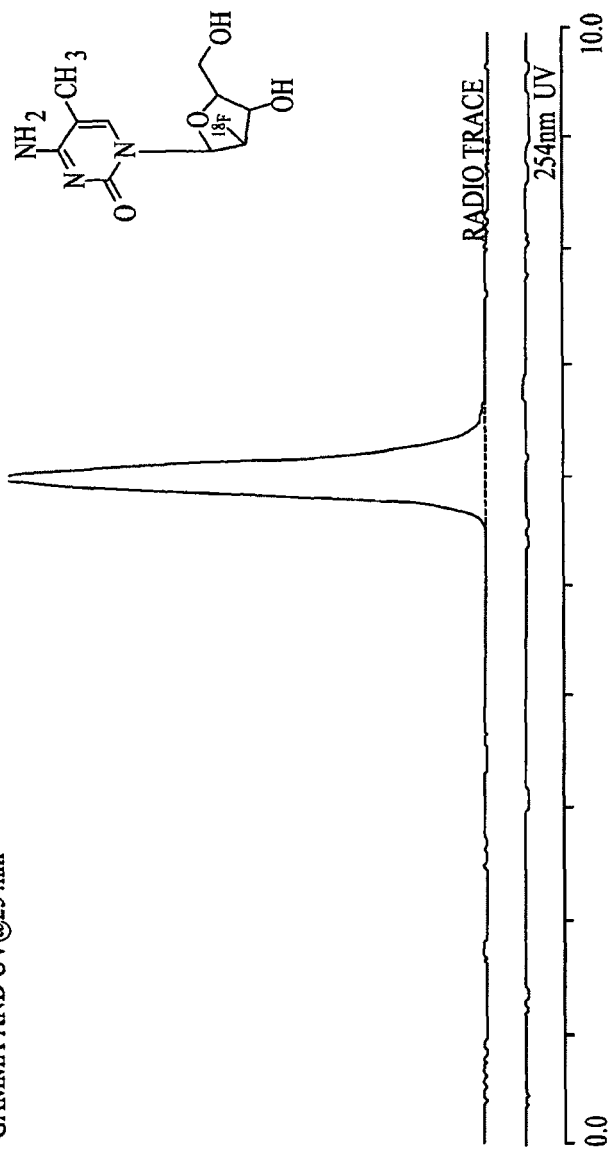
FIG. 39 is an HPLC chromatogram indicating the purity of L-[$^{18}$F] FMAC.

The chemical and radiochemical purities of L-[$^{18}$F] FMAC were determined by an analytical HPLC method using a Phenomenex Luna column (25 cm×0.46 cm, 5μ particle size). The column was eluted with 10% ethanol and 90% 50 mM ammonium acetate at a flow rate of 1.0 mL/min. The effluent from the HPLC column was passed through a UV detector (λ=254 nm) followed by a gamma radioactivity detector. The chemical and radiochemical purities of L-[$^{18}$F] FMAC prepared as described above exceeded 99.9% as shown in the enclosed typical analytical HPLC chromatogram (FIG. 39).

Analytical HPLC also was used to determine the specific activity of L-[$^{18}$F] FMAC. A range of mass vs UV absorption at 254 nm wavelength for non-radiolabeled L-FMAC was determined using the analytical HPLC method described above and the data set was used to construct a calibration graph. Using this calibration graph, the specific activity of L-[$^{18}$F] FMAC was found to be >1000 Ci/mmol.

Radionuclide Analysis

A calibrated γ-ray spectrometer was used to establish the presence of the 511 keV annihilation radiation associated with the decay of $^{18}$F isotope.

Sterility and Pyrogenicity Tests

L-[$^{18}$F] FMAC prepared as described above was tested for sterility using the standard thioglycollate medium procedure and found to be sterile.

The absence of pyrogens in the L-[$^{18}$F] FMAC preparation was verified by the standard Limulus Amebocyte Lysate (LAL) test.

Example 6

Synthesis of $^{18}$F-Clofarabine ($^{18}$F-CA)

The preparation of $^{18}$F-CA follows the reaction scheme and the description given below:

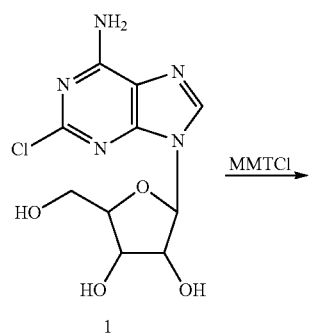

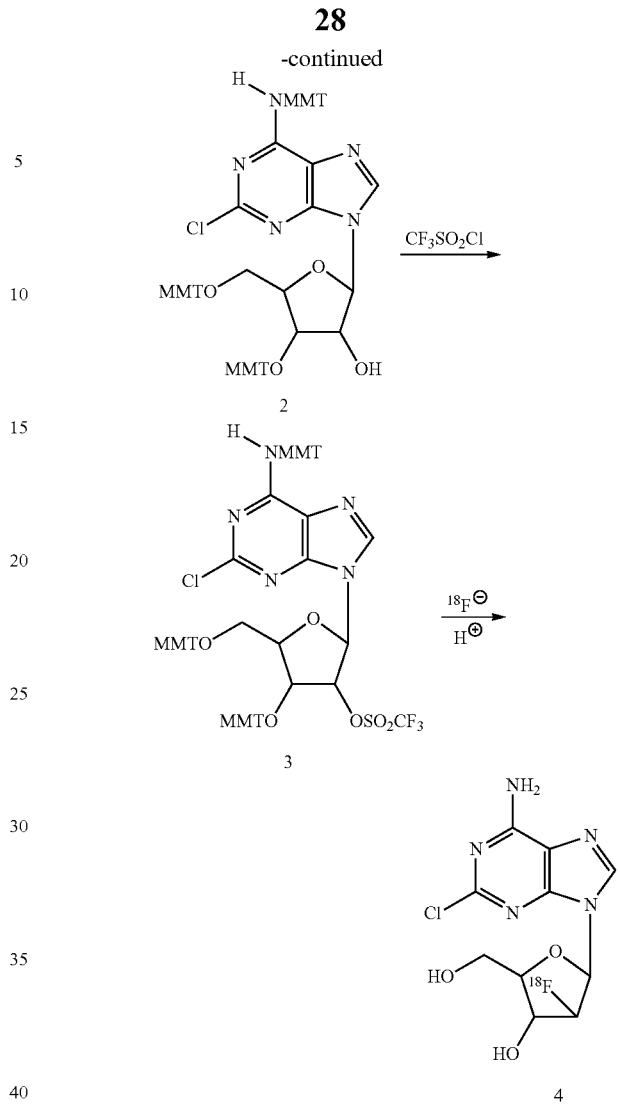

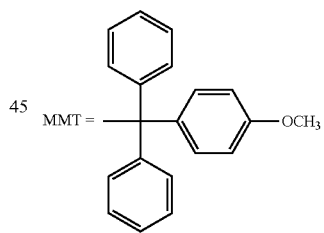

The trityl protected chloroadenosine derivative 2 was prepared by a general procedure previously reported (Pankiewicz, K. W., Krzeminski, J., Cizewaki, L. A., Ren, W.-Y., and Watanabe, K. A. "A Synthesis of 9-(2-Deoxy-2-fluoro-β-D-arabinofuranosyl)adenine and Hypoxanthine. An Effect of C3'-Endo to C2'-Endo Conformational Shift on the Reaction Course of 2'-Hydroxyl Group with DAST" *J. Org. Chem.*, 57, pp 553-559 (1992)) 2-chloroadenosine (1) (9.2 mmol), 4-dimethylaminopyridine (9.2 mmol) and monomethoxytrityl chloride (32.4 mmol) were placed in a dry 250 mL round bottom flask under argon and 80 mL of dry pyridine was added. The mixture was stirred at 90° C. for 18 h. Pyridine was evaporated in rotary evaporator and the last traces of it were azeotropically removed with toluene. The residue was dissolved in dichloromethane and washed with water. The organic layer was dried with Na$_2$SO$_4$, filtered and evaporated. The crude product was subjected to silica gel column chromatography with 25% ethyl acetate in hexane as the eluent to isolate pure hydroxy product 2. The triflate 3 was prepared from the corresponding hydroxy derivative 2 as follows: The hydroxy compound 2 (0.1 mmol) was dissolved in 3 mL of dichloromethane under argon and 4-dimethylaminopyridine (0.18 mmol) was added. The solution was cooled in an ice bath at 0° C. for 10 min. Triflyl chloride (0.02 mL) was then added and the reaction mixture was gradually warmed to room temperature and stirred for 3 h. The reaction mixture was diluted with 10 mL of dichloromethane and washed with water. The organic layer was dried with Na$_2$SO$_4$. Evaporation of dichloromethane gave an oily residue, which was purified by silica gel column chromatography using 30% ethyl acetate in hexane as eluent provided the pure triflate derivative 3.

The radiosynthesis was carried out using three of the robotic reaction modules of FIGS. 1-4. No-carrier-added [$^{18}$F]fluoride ion was produced by 11 MeV proton bombardment of 98% enriched [$^{18}$O]water in a silver target body using a RDS-112 cyclotron. The aqueous [$^{18}$F]fluoride ion was treated with a solution of K$_2$CO$_3$ (1 mg) and Kryptofix 2.2.2 (10 mg) dissolved in water (0.04 mL) and acetonitrile (0.75 mL) mixture. The solution was evaporated at 115° C. with a stream of nitrogen gas. The residue was dried by the azeotropic distillation with acetonitrile (3×0.5 mL). The triflate precursor 3 (10 mg) dissolved in 1 mL of acetonitrile was added to the dried K$^{18}$F/Kryptofix complex and reacted at 125° C. for 25 min in a sealed reaction vessel. The reaction mixture was cooled to room temperature and passed through a small cartridge of silica gel. The cartridge was eluted with 4×2 mL of ethyl acetate. The ethyl acetate was evaporated to dryness and the residue was then dissolved in 0.5 mL of acetonitrile. One mL of 1M HCl was added to the acetonitrile solution and heated at 100° C. for 5 min. The reaction mixture was diluted to a total volume of 3 mL with a solution of 15% ethanol and 85% 25 mM ammonium acetate in water and injected into a semi-preparative HPLC column (Phenomenex Gemini C-18 column; 25×1 cm) and eluted with a mobile phase of 15% ethanol and 85% 25 mM ammonium acetate in water at a flow rate of 5.0 mL/min. The effluent from the column was monitored with an UV detector (λ=263 nm) and a gamma radioactive detector. The chemically and radiochemically pure $^{18}$F-labeled product 4 with retention time between 11 and 13 min isolated in 10-15% radiochemical yield was made isotonic by dilution with sterile saline solution which also decreased the concentration of ethanol to <10%. The solution was then sterilized by passing through a Millipore sterilizing filter (0.22 μm) into a sterile multi-dose vial.

Chemical and Radiochemical Quality Control

Figure 40:
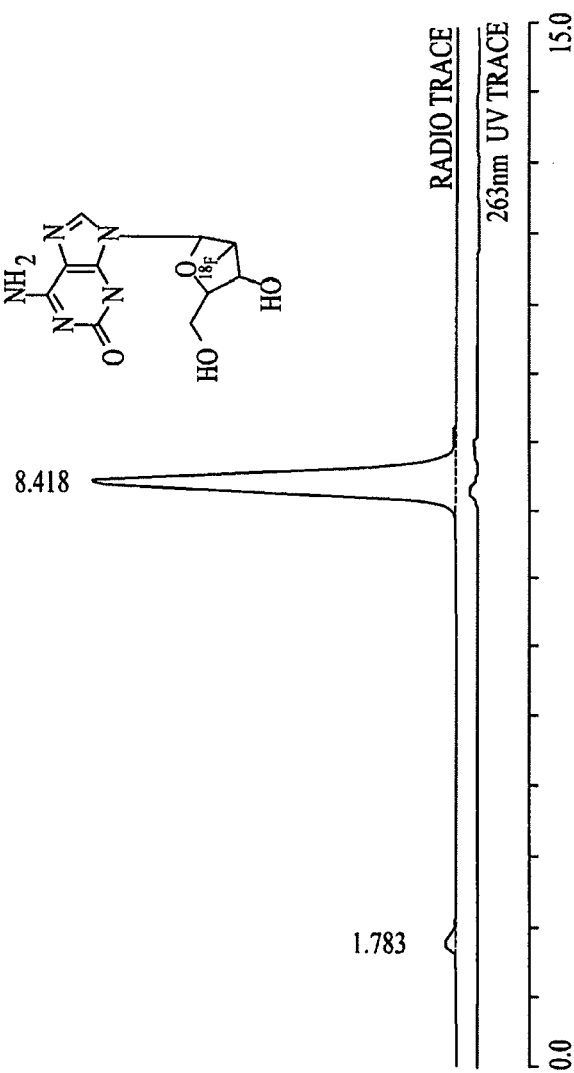
FIG. 40 is an HPLC chromatogram indicating the purity of [$^{18}$F]-CA.

The chemical and radiochemical purities of $^{18}$F-CA, as synthesized above, were determined by an analytical HPLC method using a Phenomenex Luna column (25 cm×0.46 cm, 5μ particle size). The column was eluted with 15% ethanol and 85% 25 mM ammonium acetate at a flow rate of 1.5 mL/min. The effluent from the HPLC column was passed through a UV detector (λ=263 nm) followed by a gamma radioactivity detector. The chemical and radiochemical purities of $^{18}$F-CA prepared as described above exceeded 97% as shown in the analytical HPLC chromatogram (FIG. 40).

Radionuclide Analysis

A calibrated γ-ray spectrometer was used to establish the presence of the 511 keV annihilation radiation associated with the decay of $^{18}$F isotope.

Sterility and Pyrogenicity Tests $^{18}$F-CA prepared as described above was tested for sterility using the standard thioglycollate medium procedure and found to be sterile.

The absence of pyrogens in the $^{18}$F-CA preparation was verified by the standard Limulus Amebocyte Lysate (LAL) test.

The examples above illustrate the utility of the disclosed modular systems are not intended to limit the scope of the invention and are merely representative of various capabilities of the system.

For example while the use of sealing plugs for each reaction vessel is illustrated, each reaction vessel may have remotely controlled valved ports built therein and feed materials may be delivered through remotely controlled manifolds attached to each vessel. Still further, each reaction vessel may include remotely controlled heaters and coolers integral therewith.

Example 7

Preparation of [$^{18}$F]-fluoro-4-nitrobenzene ([$^{18}$F]FNB) in the Integrated System, Including RDM, PRM and CPM (FIG. 26)

Cleaning and Drying 5-10 ml of H$_2$O was loaded into each reservoir in the RDM and the CPM and then transferring out through the manifold, delivery tubing and transfer tubing to waste. Using 5-10 ml of ethanol and acetone, the above process was repeated twice. Finally, all air valves and liquid valves in the RDM and the CPM and the reservoirs, channels, and tubings were dried.

Preloading of Reagents and Solvents

Non-radioactive reagents were preloaded into the corresponding reservoirs for the RDM and the CPM. The reagent configuration of RDM is as follows, 1,4-dinitrobenzene (DNB, 4 mg) in 0.5 ml of DMSO loaded in reservoir #3, 1 ml of H$_2$O in reservoir #5, 1 ml of H$_2$O in reservoir #6 and 1 ml of anhydrous MeCN in reservoir #8. Reservoir #2, #4 and #7 are empty. Reservoir #1 is used for loading $^{18}$F ion at a later time. The reagent configuration of CPM is as follows, 10 ml of H$_2$O in reservoir C, 10 ml of H$_2$O in reservoir A, 2 ml of methanol in reservoir D. The purification cartridge (stara C18, 30 mg) was preconditioned with 10 ml of ethanol and H$_2$O in the corresponding position of CPM.

Production and Activation of [$^{18}$F]Fluoride.

No-carrier-added [$^{18}$F]F-ion was obtained from the nuclear reaction $^{18}$O(p, n)$^{18}$F by irradiation of 97% $^{18}$O-enriched water with an 11 MeV proton beam using RDS-112 cyclotron (Siemens). 50-100 μl (10~30 μCi) of aqueous [$^{18}$F]F-ion solution in [$^{18}$O]H$_2$O was mixed with 20 mg of Kryptofix$_{222}$ (K$_{222}$), 26 μl of 1M of aqueous K$_2$CO$_3$ solution and 1 ml of anhydrous MeCN, loaded into reservoir #1 in RDM using a syringe manually, then transferred into a reaction V-vial (Wheaton) of the PRM through the delivery tubing in RDM. The mixed solution was heated at 110° C. for 5 min with hot air blowing and vacuum suction to remove the water by azeotropic evaporation until dry. After compressed-air cooling down to room temperature, 1 ml of anhydrous MeCN in reservoir #8 was delivered into the. The azeotropic evaporation was repeated once using the same condition as above. After a final addition of anhydrous MeCN, reactor heating and vacuum anhydrous K$_{222}$/[$^{18}$F]F complex.

Radiosynthesis and Purification of [$^{18}$F]FNB.

1,4-Dinitrobenzene solution in DMSO in reservoir #3 of RDM was delivered into the reaction vial. The reaction mixture was heated at 145° C. for 8 min to perform the radiofluorination of precursor and produce the labeled product [$^{18}$F]FNB. After cooling down to room temperature, 1 ml of H$_2$O in reservoir #5 was delivered into the vial to dilute the reaction mixture. The diluted mixture was transferred into reservoir C in the CPM to dilute further. 1 ml of H$_2$O in reservoir #6 of the RDM was delivered into the reaction vial to wash and obtain the residual reaction mixture, then transferred into reservoir C in the CPM. The diluted reaction mixture was passed through the cartridge and the elution was directed into a waste vial. The cartridge was washed using 10 ml of H$_2$O in reservoir A of the CPM. Finally, [$^{18}$F]FNB was eluted out using 2 ml of MeOH in reservoir D of CPM and collected in the product vial.

Quality Control of [$^{18}$F]FNB.

The total activity of [$^{18}$F]FNB solution in methanol was measured by dose calibrator and its radiochemical purity was checked by radio-TLC and radio-HPLC for the purpose of quality control. The radio-HPLC spectrum is shown in FIG. 33. The sample was spotted on a TLC plate, which was developed in pure CH$_2$C$_{12}$ and scanned by radio-TLC scanner. The sample was also injected into the HPLC to analyze, which was run using MeCN/H$_2$O (V/V 50/50) with 0.2% TFA as a mobile phase at the flow rate of 1 ml/min. The HPLC-System comprises a K2501 UV detector (Knauer), B-FC-1000 radiodetector (Bioscan), 501 pump (Knauer) and Luna column (5 m C18(2) 100 A, 250×4.6 mm) (Phenomenex) and Gina box (Raytest) for data acquisition and interpretation. 254 nm was selected as the UV detection wavelength.

Example 8

Preparation of 1$^{18}$F12-fluoro-2-deoxy-D-glucose ([$^{18}$F]FDG) in the Integrated System, Including RDM, PRM and CPM (FIG. 26)

Cleaning and Drying the System.

The procedure is the same as that for [$^{18}$F]FNB

Preloading of Reagents and Solvents.

The procedure is substantially the same as that for [$^{18}$F]FNB, except for the reagents and cartridge described as follows. For the reagent configuration of the RDM, mannose triflate (25~30 mg) in 1.5 ml of anhydrous MeCN was loaded into reservoir #3, 2 ml of aq. HCl (1M) was placed in reservoir #5, 1 ml of H$_2$O was placed into reservoir #6 and 1 ml of anhydrous MeCN was placed in reservoir #8. Reservoir #2, #4 and #7 were empty. Reservoir #1 was reserved for loading $^{18}$F ion. For the reagent configuration of CPM, 10 ml of H$_2$O was placed in reservoir C; reservoir A and D were empty. The purification cartridge consisted of a cation and anion resin mixed column, C18 and Al$_2$O$_3$ column preconditioned with 10 ml of ethanol and H$_2$O in the corresponding position of CPM.

Production and Activation of $^{18}$F Ion.

The procedure is same as that for [$^{18}$F]FNB.

Radiosynthesis and Purification of [$^{18}$F]FDG.

Figure 34:
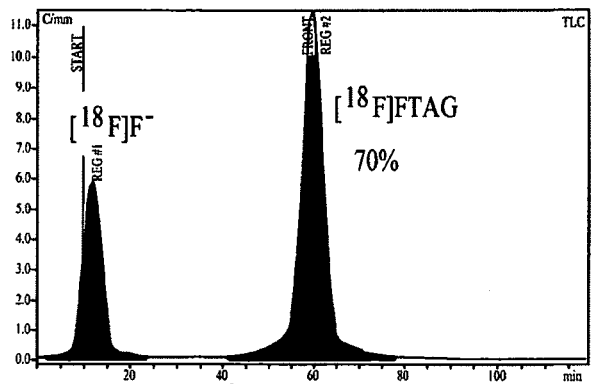
FIGS. 34, 35, and 36 are radio-TLC spectrums for three stages in the production of [$^{18}$F] FDG with FIG. 34 showing the spectrum after fluorination, FIG. 35 showing the spectrum after hydrolysis and FIG. 36 showing the spectrum after purification.
Figure 35:
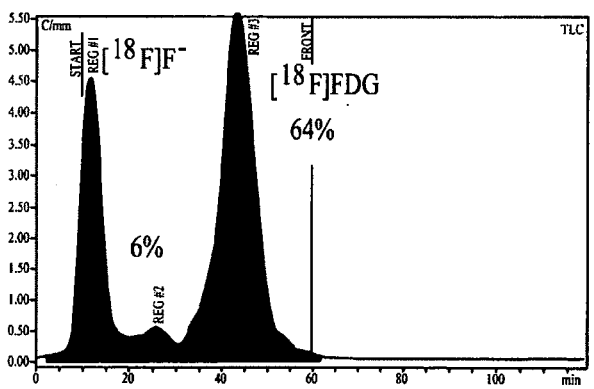

Triflate precursor in MeCN in reservoir #3 of RDM was delivered into the reaction vial. The reaction mixture was heated at 100° C. for 4 min to perform the radiofluorination of the precursor to produce the labeled product [$^{18}$F]F-TAG, the radio HPLC of this intermediate is shown in FIG. 34. The heating was applied for additional 4 min to remove the solvent MeCN. After cooling down to room temperature, 1.5 ml of aq. HCl solution in reservoir #5 was delivered into the vial and heated at 100° C. for 10 min to produce the hydrolyzed product (See FIG. 35 for radio-HPLC). After cooling down, The reaction mixture was transferred into reservoir C in CPM to dilute further. 2 ml of H$_2$O in reservoir #6 was delivered into the reaction vial to wash and obtain the residual reaction mixture which was then transferred into reservoir C in the CPM. The diluted reaction mixture was passed through the purification cartridge and the elution was delivered to the product vial.

Figure 36:
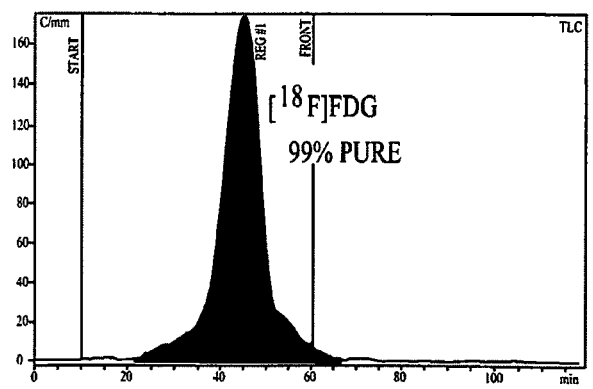

Quality control of [$^{18}$F]FDG—The total activity of [$^{18}$F]FDG solution was measured by dose calibrator and its radiochemical purity was checked by radio-TLC for quality control (See FIG. 36). The sample was spotted on TLC plate, which was developed in mixed solvent of MeCN/H$_2$O (95/5) and scanned by radio-TLC scanner.

Example 9

Preparation of N-succinimidyl-4-[$^{18}$F]fluoro benzoate ([$^{18}$F]SFB) in the Integrated System, Including RDM, MRM and CPM The preparation of [$^{18}$F]SFB follows the reaction scheme and the description given below:

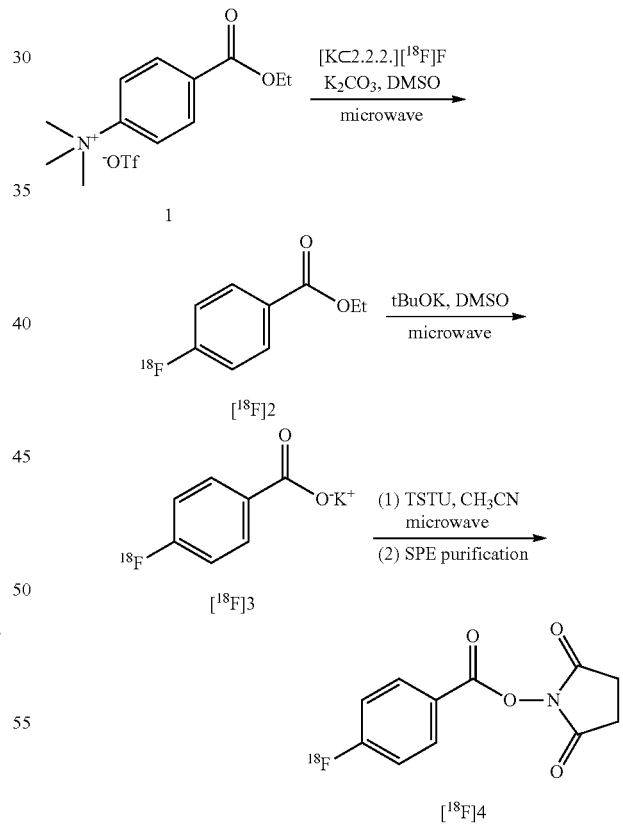

System Configuration.

A 5 mL V-vial with PEEK adapter lid containing seven tubing ports was installed in a microwave module, comprising a CEM microwave system and an auxiliary controller. Three outputs of an RDM (configured with dedicated outputs for each reagent) was connected to three of the ports on the vial adapter. In this synthesis, not all reagents were pre-stored on the RDM; rather they were injected via tubing from outside the shielded environment when needed. Four ports of the vial adapter were connected to the microwave reactor auxiliary controller. This controller performs the following functions: open a vent when adding reagents, apply vacuum and nitrogen stream during evaporation, and apply pressure to transfer product out of reactor via the dip tube. The dip tube was connected to the input of the CPM for purification of the final product. Reservoir C (diluent) of the CPM was loaded with 8 mL of a 5 vol. % solution of acetic acid in water. Reservoir A (wash) was loaded with 10 mL of the mixed solvent MeCN/H$_2$O (v/v 2:1). Reservoir D (eluent) was filled with 3 mL of diethyl ether. A Merck EN cartridge (200 mg, conditioned with 10 mL of ethanol and 10 mL of a 5 vol. % solution of acetic acid in water) was installed.

Production and Activation of [$^{18}$F]Fluoride.

An aliquot of aqueous [$^{18}$F]fluoride solution (50~100 µL, 1850~3700 MBq) was added to Kryptofix 2.2.2 (10 mg, 26.6 µmol) and 13 µL of a 1 M potassium carbonate solution. The mixture was diluted with 0.9 ml of dry acetonitrile and transferred to the reactor via RDM position 1. With vacuum applied, the solvent was evaporated at a microwave power of 20 W for 3 min. Azeotropic drying was repeated with addition of 1 mL acetonitrile through RDM position 1.

Preparation of 4-[$^{18}$F]Fluorobenzoic Acid ([$^{18}$F]3).

A solution of 1 (ca. 2.5 mg, 7.0 µmol) in dry DMSO (300 µL) was added to the vial containing the dried [K⊂2.2.2][$^{18}$F]F salt through RDM position 2. With reaction vial sealed (all valves closed), stirring and air cooling activated, the reaction was completed in 1 min with a microwave power of 50 W. A solution of potassium tert.-butoxide (ca. 10 mg, 89.1 µmol) in DMSO (300 µL) was then added through RDM position 2. The second (deprotection) step of the reaction was carried out with the vial sealed, stirring and air cooling activated, under a microwave power of 40 W for 1 min to yield [$^{18}$F]3.

Preparation and Purification of N-Succinimidylester 4-[$^{18}$F]Fluorobenzoate ([$^{18}$F]4).

To [$^{18}$F]3 in DMSO a solution of TSTU (30 mg, 100.0 µmol) in acetonitrile (2.5 mL) was added through RDM position 3. Linkage of the succinimidyl moiety to [$^{18}$F]3 was performed with air cooling and stirring at a microwave power of 30 W for 2 min. The reaction mixture was transferred to the CPM for dilution. In the CPM, the product was caused to flow through the installed Merck EN cartridge, followed by the wash solution, and then nitrogen to dry the cartridge. The eluent was caused to flow through the cartridge to recover the product into a collection vial. After a synthesis time of 35~40 min 370~1110 MBq (RCY: 20~30%) of n.c.a. N-succinimidyl-4-[$^{18}$F]fluorobenzoate was produced (radiochemical purity>98%).

The various descriptions set forth above of the reaction module and the other modules used therewith, referred to as special function modules, and the components comprising the modules are provided as examples thereof and are not intended to limit the various components of the modules, the arrangement of the modules in an assembled modular reaction system, the use of the modules or other supplemental components which made be added thereto. Further, while some of the examples show systems with only one reaction module and one or more different special function modules it is contemplated that the modular chemical reaction system incorporating features of the invention may include multiple reaction modules as well as multiples of the various specialty modules. For example, the system can include one or more reaction modules, one or more reagent storage and delivery modules, one or more purification modules, one or more quality control and analysis modules, one or more chemical transfer modules, one or more aliquotting modules, one or more concentrating or drying modules, one or more chemical concentrating modules and one or more radiation counting modules. Further, it is contemplated that additional special function modules may be added to the system to further expand the capability of the system. Still further, the various modules can be arranged to operate in series or in parallel as required to produce one or more exit streams of the desired end product.

It is further contemplated that the reaction modules as well as the special function modules may include any desired sensors (i.e., temperature, pressure, pH, radiation counters, etc) and analytical probes (i.e., IR, UV, specialty probes for various chemical constituents, etc) for conducting process analysis during a reaction in the system as well as transmission means (i.e., hard wired, fiber optics, telemetry, etc) for delivery of the sensor or probe output to a remotely located controller or monitor. Other components of the various modules can include, pumps, valves, stirring systems, liquid separation systems or other components, all remotely controlled, as are typically required to conduct an automated chemical reaction. While each of the reaction modules and special function modules include the sensors, probes, and controllers necessary for independent operation of that module, they are also configured so that all of the modules comprising a reaction system, the components thereof and the functions thereof can be monitored and controlled by a single system monitor and controller such as provided by a general purpose computer.

It is also contemplated that one or more components of the reaction module are moveable, using a remote located control system to, for example, allow the system operator to provide or remove heating or cooling to the reaction vessel or vial or to allow addition or removal of materials to the reaction vessel or vial. In a like manner movement of the components in the special function modules may be provide and controlled. Still further, movement of the various modules in relationship to the other modules is also contemplated so that various different modules can be plugged together to provide the desired assembled reaction system. Video capability is provided so that operation can be observed.

As set forth above, the assembly and operation of the modular chemical product system and each the modules comprising that system are controlled, monitored, observed and recorded using various audio, visual, and electronic means so that the operation of the system can also be reviewed and duplicated.

We claim:

1. A method of performing radiochemistry synthesis comprising:
   providing a vial having an upper rim, the vial configured to hold one or more reactants or reactant products of the radiochemistry synthesis;
   providing a reactor vessel having a heating element and a thermally-conductive heat transfer block, the vial being contained within the thermally-conductive heat transfer block;
   providing a stationary fluidic interface disposed above the reactor vessel and vial and comprising a plurality of elastomeric stoppers, wherein at least one of the elastomeric stoppers comprises a completely sealed surface and at least one of the elastomeric stoppers comprises a port fluidically coupled to tubing;

providing a horizontal actuator coupled to the reactor vessel and configured to move the reactor vessel along a substantially horizontal axis of motion;

providing a vertical actuator coupled to the reactor vessel and configured to move the reactor vessel along a substantially vertical axis of motion;

providing a motion controller operatively coupled to the horizontal actuator and the vertical actuator; and wherein the motion controller operates in accordance with a program to selectively seal the upper rim of the vial against the plurality of elastomeric stoppers.

2. The method of claim 1, wherein the program is pre-programmed using a control unit associated with a computer.

3. The method of claim 1, wherein the tubing is connected to a purification unit and contents of the vial are transferred from the vial to the purification unit.

4. The method of claim 3, wherein a dip tube extends from the stationary fluidic interface and into the vial when the upper rim of the vial is sealed against the plurality of elastomeric stoppers.

5. The method of claim 1, wherein the tubing is connected to a source of vacuum and the source of vacuum transfers contents out of the vial.

6. The method of claim 1, wherein the tubing is connected to a source of inert gas, wherein the source of inert gas is introduced into the vial.

7. The method of claim 1, wherein the tubing is connected to one or more reagent sources, wherein at least one reagent is introduced into the vial.

8. The method of claim 1, further comprising measuring the radioactivity of the reactant products of the radiochemistry synthesis with a radiation sensor.

9. The method of claim 1, wherein the stationary fluidic interface comprises a first elastomeric stopper in a first position that includes a conduit that extends through the first elastomeric stopper and second elastomeric stopper in a second position that comprises the completely sealed surface.

10. The method of claim 9, wherein the second elastomeric stopper comprises a chemically inert gasket.

11. The method of claim 1, wherein the stationary fluidic interface comprises a first elastomeric stopper in a first position that includes tubing that extends through the first elastomeric stopper, a second elastomeric stopper in a second position that comprises the completely sealed surface, and third elastomeric stopper that includes a dip tube that extends through the third elastomeric stopper.

12. The method of claim 11, further comprising sealing the upper rim of the vial against the first elastomeric stopper and adding reagents into the vial.

13. The method of claim 12, wherein the reagents comprise an aqueous F-18 solution, a dry organic solvent, a phase transfer agent, and a carbonate.

14. The method of claim 12, further comprising mixing the contents of the vial by bubbling an inert gas in the vial.

15. The method of claim 11, further comprising sealing the upper rim of the vial against the second elastomeric stopper and heating the contents of the vial.

16. The method of claim 11, further comprising sealing the upper rim of the vial against the third elastomeric stopper and transferring the contents of the vial out of the vial.

* * * * *